(12) United States Patent
Grainger et al.

(10) Patent No.: US 8,618,283 B2
(45) Date of Patent: Dec. 31, 2013

(54) LIGAND LIBRARIES FOR SCREENING GPCRS

(75) Inventors: David J Grainger, Cambridge (GB); David John Fox, Coventry (GB)

(73) Assignee: Cambridge Enterprise Limited, Cambridge (GB)

( * ) Notice: Subject to any disclaimer, the term of this patent is extended or adjusted under 35 U.S.C. 154(b) by 0 days.

(21) Appl. No.: 13/289,542

(22) Filed: Nov. 4, 2011

(65) Prior Publication Data

US 2012/0046198 A1 Feb. 23, 2012

Related U.S. Application Data

(63) Continuation of application No. 11/815,928, filed as application No. PCT/GB2006/000475 on Feb. 10, 2006, now abandoned.

(30) Foreign Application Priority Data

Feb. 11, 2005 (GB) .................................. 0502914.5

(51) Int. Cl.
*C40B 30/00* (2006.01)
*A61K 38/00* (2006.01)

(52) U.S. Cl.
USPC ............... 540/575; 506/7; 514/218; 514/20.6

(58) Field of Classification Search
None
See application file for complete search history.

(56) References Cited

U.S. PATENT DOCUMENTS

2004/0009966 A1 * 1/2004 Wos et al. ................ 514/211.03
2008/0261948 A1 10/2008 Grainger

FOREIGN PATENT DOCUMENTS

| WO | 96/03429 A1 | 2/1996 |
| WO | 03/103677 A1 | 12/2003 |
| WO | 2004/031154 A1 | 4/2004 |
| WO | 2004/092166 A2 | 10/2004 |

OTHER PUBLICATIONS

PCT Application No. PCT/GB2006/000475: International Preliminary Report on Patentability mailed Aug. 23, 2007, 9 pgs.
PCT Application No. PCT/GB2006/000475: International Search Report mailed Jun. 1, 2006, 5 pgs.
Breitholle, E. G., et al., "Synthesis of Some Dehydrophenylalanine Peptides", Journal of Organic Chemistry. 41(8) (1976), 1344-1349.
Corelli, P., et al., "Cyclic Dipeptides. A Stereocontrolled Synthesis of (2S, 3R, 6R)- and (2R, 3R, 6R)-6-tert-butoxycarbonylamino-3-methoxycarbonyl-2-methyl-5-oxoperhydro-1 ,4-thiazepine", Tetrahedron: Asymmetry, 5(8), (1994), 1469-1472.
Klar, B., et al., "Asymmetric Induction Effects in the Preparation of Penicillin-Analogous Thiazepines", Liebiqs Annalen/Recueil (8), (1997), 1711-1718.
Lampariello, L. R., et al., "Solid-Phase Synthesis of Conformationally Constrained Peptidomimetics Based on a 3,6-Disubstituted-1 ,4-diazepan-2,5-dione Core.", Journal of Organic Chemistry 68(20), (2004), 7893-7895.
Sjoberg, B., et al., "On the Role of "Cyclic Cysteinylvaline" in Penicillin Biosynthesis", Tetrahedron Letters 6(4), (1965), 281-286.
Yanagisawa, H., et al., "Angiotensin-Converting Enzyme Inhibitors: Perhydro-1,4-thiazepin-5-one Derivatives", J. Med. Chem. 30(11) (1987),1984-1991.
"Unnatural Amino Acids: Tools for Drug Discovery", ChemFiles, vol. 4(5), Sigma-Aldrich Chemical Company, (2004).

* cited by examiner

*Primary Examiner* — Christopher M Gross
(74) *Attorney, Agent, or Firm* — VLP Law Group LLP; Richard G. A. Bone

(57) ABSTRACT

The invention provides compounds of general formulae (I)-(IV) or pharmaceutically acceptable salts thereof:

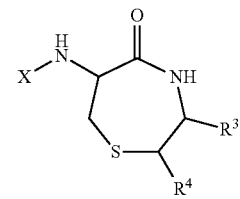

(I)

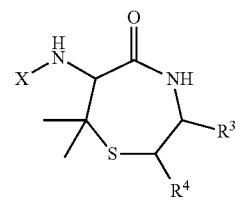

(II)

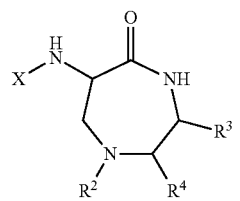

(III)

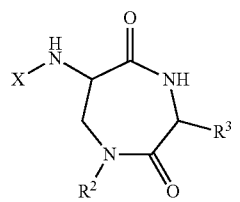

(IV)

The invention also provides methods of preparing the compounds, pharmaceutical compositions comprising the compounds and use of the compounds for the preparation of medicaments intended to modulate the activity of one or more members of the G-protein coupled receptor (GPCR) class. Compounds of the invention may be used to create a compound library for use in screening for agents which modulate signalling through GPCRs.

12 Claims, No Drawings

LIGAND LIBRARIES FOR SCREENING GPCRS

CLAIM OF PRIORITY

This application claims the benefit of priority under 35 U.S.C. §120 to, and is a continuation of U.S. patent application Ser. No. 11/815,928 filed Apr. 15, 2008 (now abandoned), which application is the U.S. national stage under 35 U.S.C. §371 of International Application Number PCT/GB2006/000475, having an international filing date of Feb. 10, 2006, which claims benefit of priority to United Kingdom Patent Application Number 0502914.5, filed Feb. 11, 2005, which applications are incorporated herein by reference.

SUMMARY

The invention relates to the generation of a library of compounds enriched in agonists and antagonists for members of the G-protein coupled class of receptors (GPCRs).

Members of the G-protein coupled receptor (GPCR) class of membrane proteins (also known as seven-transmembrane spanning or 7TM receptors and serpentine receptors) mediate cellular signalling in response to a very wide variety of extracellular signals, including hormones, neurotransmitters, cytokines and even environmental substances such as odours and tastes. In response to the ligand interacting with the extracellular portion of the receptor (most usually the N-terminal tail of the receptor protein), the receptor is converted temporarily to an activated state (this conversion is usually designated R+L→R*L where R is the inactive receptor, R* is the activated receptor and L is the ligand).

The activated (or R*) conformation of the receptor is then able to interact with a member of the G-protein family. The G-proteins are a large family of trimeric intracellular proteins which bind guanine nucleotides. On interacting with the activated receptor (probably by a mechanism called "collisional coupling") the G-protein exchanges a bound guanosine diphosphate (GDP) for a guanosine triphosphate (GTP). In this GTP-bound form the G-protein trimer dissociates, yielding a free Gα subunit, and a βγ dimer. Both the Gα and βγ subunits can then participate in further signalling cascades. For example, the Gα subunit can activate the adenylate cyclase (AC) enzyme, which generates cyclic adenosine monophosphate (cAMP) from adenosine triphosphate. The βγ subunit can activate members of the PI-3-kinase family of enzymes. Ultimately, these signals can result in modulation of almost every aspect of cell behaviour, from contraction to motility, metabolism to further signalling.

The signal, once activated, is then slowly turned off by a number of mechanisms. The GTP associated with the Gα subunit is hydrolysed back to GDP, resulting in the reassociation of the Gα and βγ subunits to form the inactive trimeric GDP-bound G-protein. The GPCR itself also becomes phosphorylated on the intracellular C-terminus, preventing further interaction with G-proteins. Eventually, the bound ligand may also dissociate.

This generic signalling pathway is so central and ubiquitous in mammalian physiology that as many as 40% of licensed pharmaceuticals have a GPCR among their molecular targets. Similarly, bacteria have evolved to target G-protein signalling in order to disrupt host physiology and immunity: *Vibrio cholerae* (the organism responsible for cholera), for example, makes a protein known as cholera toxin which irreversibly inhibits the Gα subunit of a widely distributed G-protein called $G_s$. Similarly, *Bordetella pertussis* (the organism responsible for Whooping Cough) makes a protein known as Pertussis toxin which has a similar effect on a different G-protein, $G_i$.

One approach to identifying pharmaceuticals which will modulate GPCR signalling has been to screen very large random compound libraries for the ability to interfere with ligand binding to membrane preparations containing recombinant or purified GPCRs. In such high throughput screens, various methods have been adopted to facilitate the detection of binding. For example, in scintillation proximity assays, the binding of a radiolabelled ligand to the receptor brings the radionucleide into proximity with a scintillant molecule bound to the receptor—as the nucleide decays, light is emitted which can be detected and quantified. Alternatively, the ligand can be fluorescently labelled and the binding detected by fluorescence polarisation (dependent on the reduced rotational degress of freedom of the fluorescent tag when the ligand is immobilised on binding to the receptor).

While these techniques have been successful in some instances, and yielded lead compounds which have subsequently been developed as human pharmaceuticals (for example, the $5HT_3$ receptor antagonist Ondansetron, used to treat migraine headaches), there remain large numbers of GPCRs for which few, if any, suitable non-peptide agonist or antagonist compounds have been identified, despite intensive screening across the pharmaceutical industry. For example, there are few specific non-peptide antagonists for the chemokine receptor family of GPCRs, and no agonists. Since chemokines play a central role in immune regulation, such molecules would be expected to be extremely valuable pharmaceuticals with immunomodulatory properties useful in treating a wide range of diseases with an inflammatory component.

Two factors limit the likely success of random screening programmes: firstly, there is a very large compound space to be screened, and even with the best available high throughput technology and the best combinatorial chemistry approaches to generating diverse libraries, only a small fraction of all possible molecular structures can be investigated. Secondly, even when leads have been successfully identified the core pharmacophores are often not suitable for use in vivo—the lead compound and its analogs may be simply too toxic.

Another major problem with such "negative screening" paradigms (where you detect the ability of the test library to block binding of a labelled ligand) is that most of the leads identified are receptor antagonists. Few of the leads have any agonist activity (as expected—agonist activity requires the ability to bind to and then convert the receptor to the activated conformation, whereas antagonist actively merely requires the ability to bind to the receptor or ligand in such a way as to prevent their interactions) and generating analogs of the initial antagonist leads to convert them to agonists is a "hit and miss" affair with very low success rates.

One approach to circumventing this problem would be to replace the random compound library with a library of molecular structures preselected to contain a high proportion of GPCR binding compounds. Such a library would also ideally include both agonists and antagonists in similar proportion so that either could be readily located. Ideally, also, the basic molecular structures used in the library would be non-toxic.

Whether or not real libraries can be constructed which approximate these ideal properties is not at all clear. If they do, it will require the existence of a putative "ideal" GPCR substrate which would interact with many different GPCRs irrespective of their natural ligand preferences. By varying the substitution of this idealised substrate it may then be possible to impart selectivity for one receptor in the class over all the others.

Here we describe an example of such an "ideal" GPCR substrate. Based on this "ideal" substrate, we provide a range of related skeletons which can be variously substituted to generate agonists and/or antagonists at a range of different GPCRs. The invention also provides for the preparation of libraries of said substituted compounds as well as their application in a screening process in order to generate GPCR ligands with any prescribed set of specificities. In this way, it is now possible to "dial up" a GPCR ligand with a known set of properties (for example, a ligand which has agonist activity at dopamine D2 receptors at the same time as antagonist activity at serotonin $5HT_{1a}$ (receptors)). In contrast, identifying such mixed ligands serendipitously from random libraries is a very rare event.

The requirements for the generation of said libraries are: (i) the identification of the molecular motif necessary for binding to GPCRs (ii) a skeleton incorporating this molecular motif so as to retain GPCR binding, but also providing low intrinsic toxicity and good stability, pharmacokinetics and/or pharmacodynamics (iii) a facile synthetic route to generate diverse substitution of the skeleton.

The present invention is based on the ideal substrate below:

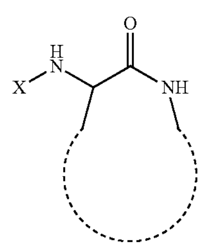

where X is R—CO— or R—$SO_2$— and R represents diverse substitution. The dotted line indicates constraint of the bond angles within the molecular motif, for example by cyclisation.

The skeletons which are provided have been designed using the wide availability of α-amino acids as starting materials in order to generate the diversity of substitution (see, for example, Unnatural Amino Acids: Tools for Drug Discovery; Sigma-Aldrich ChemFiles Vol 4 No. 6). Each of the skeletons is synthesised from the combination of two α-amino acids. The first may be selected from cysteine, penicillamine or 3-aminoalanine. Any amino acid is then paired with the first amino acid to generate the requisite diversity.

The invention provides compounds and salts thereof of general formula (I), representing the synthetic product of reactions using cysteine and a second amino acid as the starting materials:

(I)

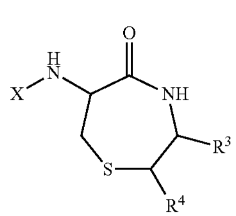

wherein
X is —CO—$(Y)_k$—$(Z)_n$ or $SO_2$—$(Y)_k$—$(Z)_n$;
k is 0 or 1;
Y is a cycloalkyl or polycyloalkyl group (such as an adamantyl, adamantanemethyl, bicyclooctyl, cyclohexyl, cyclopropyl group);
or Y is a cycloalkenyl or polycycloalkenyl group;
each Z is independently selected from hydrogen or an alkyl, haloalkyl, alkoxy, haloalkoxy, alkenyl, alkynyl, alkylamino, alkylaminoalkyl, alkylaminodialkyl, charged alkylaminotrialkyl or charged alkylcarboxylate radical of 1 to 20 carbon atoms;
or each Z is independently selected from fluoro, chloro, bromo, iodo, hydroxy, oxyalkyl, amino, aminoalkyl, aminodialkyl, charged aminotrialkyl, or carboxylate radical; and
n is any integer from 1 to m, where m is the maximum number of substitutions permissible on the cyclo-group Y.

Alternatively Z may be selected from a peptido radical, for example having from 1 to 4 peptidic moieties linked together by peptide bonds (for example a peptido radical of 1 to 4 amino acid residues).

$R^3$ and $R^4$ represent the diverse subtitutions which, together with Z, distinguish one library element from another.

This class of compounds, 6-acylamino-[1,4]thiazepan-5-ones, are described as "Thiofoxins". The key structural features of the molecules are the lactam amide in a ring system, with an amino group attached to the carbon atom next to the lactam carbonyl group (the 6-position, termed the α-carbon), and sulfur at the 1 position and $R^3$ and $R^4$ (variable) at the 3 and 2 positions of the lactam ring, respectively.

The invention also provides compounds and salts thereof of general formula (II), representing the synthetic product of reactions using penicillamine and a second amino acid as the starting materials:

(II)

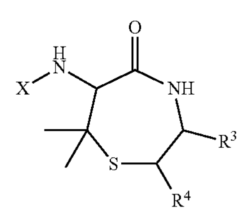

wherein:
X is —CO—$(Y)_k$—$(Z)_n$ or $SO_2$—$(Y)_k$—$(Z)_n$;
k is 0 or 1;
Y is a cycloalkyl or polycyloalkyl group (such as an adamantyl, adamantanemethyl, bicyclooctyl, cyclohexyl, cyclopropyl group);
or Y is a cycloalkenyl or polycycloalkenyl group;
each Z is independently selected from hydrogen or an alkyl, haloalkyl, alkoxy, haloalkoxy, alkenyl, alkynyl, alkylamino, alkylaminoalkyl, alkylaminodialkyl, charged alkylaminotrialkyl or charged alkylcarboxylate radical of 1 to 20 carbon atoms;
or each Z is independently selected from fluoro, chloro, bromo, iodo, hydroxy, oxyalkyl, amino, aminoalkyl, aminodialkyl, charged aminotrialkyl, or carboxylate radical; and
n is any integer from 1 to m, where m is the maximum number of substitutions permissible on the cyclo-group Y.

Alternatively Z may be selected from a peptido radical, for example having from 1 to 4 peptidic moieties linked together by peptide bonds (for example a peptido radical of 1 to 4 amino acid residues).

$R^3$ and $R^4$ represent the diverse subtitutions which, together with Z, distinguish one library element from another. $R^3$ and $R^4$ may be independently selected as any substituent group, except that $R^3$ may not be —COOH, —COOR', —COSR', or —CONR'R" where R' and R" independently are any substituent and either or both of R' and R" can be H.

This class of compounds, 6-acylamino-7,7-dimethyl[1,4]thiazepan-5-ones, are described as "Dimethylthiofoxins". The key structural features of the molecules are the lactam amide in a ring system, with an amino group attached to the carbon atom next to the lactam carbonyl group (the 6-position, termed the α-carbon), and sulfur at the 1 position and $R^3$ and $R^4$ (variable) at the 3 and 2 positions of the lactam ring, respectively.

The invention also provides compounds and salts thereof of general formula (III), representing the synthetic product of reactions using 3-aminoalanine and a second amino acid as the starting materials:

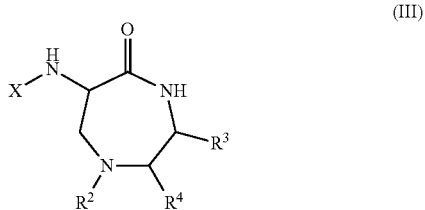

(III)

wherein:
X is —CO—$(Y)_k$—$(Z)_n$ or $SO_2$—$(Y)_k$—$(Z)_n$;
k is 0 or 1;
Y is a cycloalkyl or polycyloalkyl group (such as an adamantyl, adamantanemethyl, bicyclooctyl, cyclohexyl, cyclopropyl group);
or Y is a cycloalkenyl or polycycloalkenyl group;
each Z is independently selected from hydrogen or an alkyl, haloalkyl, alkoxy, haloalkoxy, alkenyl, alkynyl, alkylamino, alkylaminoalkyl, alkylaminodialkyl, charged alkylaminotrialkyl or charged alkylcarboxylate radical of 1 to 20 carbon atoms;
or each Z is independently selected from fluoro, chloro, bromo, iodo, hydroxy, oxyalkyl, amino, aminoalkyl, aminodialkyl, charged aminotrialkyl, or carboxylate radical; and
n is any integer from 1 to m, where m is the maximum number of substitutions permissible on the cyclo-group Y.

Alternatively Z may be selected from a peptido radical, for example having from 1 to 4 peptidic moieties linked together by peptide bonds (for example a peptido radical of 1 to 4 amino acid residues).

$R^2$, $R^3$ and $R^4$ represent the diverse substitutions which, together with Z, distinguish one library element from another.

This class of compounds, 6-acylamino-[1,4]diazepan-5-ones, are described as "Azafoxins". The key structural features of the molecules are the lactam amide in a ring system, with an amino group attached to the carbon atom next to the lactam carbonyl group (the 6-position, termed the α-carbon), and nitrogen at the 1 position and $R^3$ and $R^4$ (variable) at the 3 and 2 positions of the lactam ring, respectively. Optionally, further diversity can be generated by substitution with $R^2$ (variable) at the N1 position.

The invention also provides compounds and salts thereof of general formula (IV), representing an alternative synthetic product of reactions using 3-aminoalanine and a second amino acid as the starting materials:

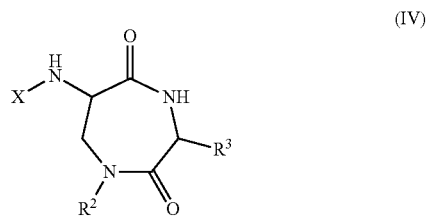

(IV)

wherein
X is —CO—$(Y)_k$—$(Z)_n$ or $SO_2$—$(Y)_k$—$(Z)_n$;
k is 0 or 1
Y is a cycloalkyl or polycyloalkyl group (such as an adamantyl, adamantanemethyl, bicyclooctyl, cyclohexyl, cyclopropyl group);
or Y is a cycloalkenyl or polycycloalkenyl group;
each Z is independently selected from hydrogen or an alkyl, haloalkyl, alkoxy, haloalkoxy, alkenyl, alkynyl, alkylamino, alkylaminoalkyl, alkylaminodialkyl, charged alkylaminotrialkyl or charged alkylcarboxylate radical of 1 to 20 carbon atoms;
or each Z is independently selected from fluoro, chloro, bromo, iodo, hydroxy, oxyalkyl, amino, aminoalkyl, aminodialkyl, charged aminotrialkyl, or carboxylate radical; and
n is any integer from 1 to m, where m is the maximum number of substitutions permissible on the cyclo-group Y.

Alternatively Z may be selected from a peptido radical, for example having from 1 to 4 peptidic moieties linked together by peptide bonds (for example a peptido radical of 1 to 4 amino acid residues).

$R^2$ and $R^3$ represent the diverse substitutions which, together with Z, distinguish one library element from another.

This class of compounds, 6-acylamino-[1,4]diazepan-2,5-diones, are described as "Amidofoxins". The key structural features of the molecules are the lactam amide in a ring system, with an amino group attached to the carbon atom next to the lactam carbonyl group (the 6-position, termed the α-carbon), nitrogen at the 1 position, a carbonyl group at the 2 position with $R^3$ (variable) at the 3 position of the lactam ring. Optionally, further diversity can be generated by substitution with $R^2$ (variable) at the N1 position.

The α-carbon of these Thiofoxins, Dimethylthiofoxins, Azafoxins, and Amidofoxins is asymmetric and consequently, the compounds according to the present invention have two possible enantiomeric forms, that is, the "R" and "S" configurations. The present invention encompasses the two enantiomeric forms and all combinations of these forms, including the racemic "RS" mixtures. With a view to simplicity, when no specific configuration is shown in the structural formulae, it should be understood that the two enantiomeric forms and their mixtures are represented.

The compounds of general formulae (I), (II), (III) and (IV) are all N-substituted on the exocyclic amine group. The N-substitutent is either a carbon amide or a sulfonamide. The geometry of the carbon atom next to the carbonyl of the carbon amide or the sulfoyl group of the sulfonamide (the "key" carbon) may be important for the bioactivity of the molecule. The nature of this N-substituent may be such that the ring or rings of Y constrain the bond angles at the "key"-carbon to be essentially tetrahedral (i.e. sp3 hybrid bonds). Any substituent Z may be a substituent at any permissible position on the ring or rings of the cyclo-group Y. In particular it is to be noted that the invention includes compounds in which the "key carbon" is both part of the cyclo group and is itself substituted. The definition of $(Z)_n$ encompasses compounds of the invention with no substitution (i.e., Z=hydrogen), compounds of the invention with mono substitution (i.e. Z is not hydrogen and n=1), and also multiple substitution (i.e. at least two Z groups are not hydrogen and n=2 or more).

One major advantage of the compounds of the invention is that the diverse library elements may be readily synthesised readily synthesised from two different α-amino acids. α-amino acids represent an ideal starting material for diversity-oriented synthesis since a wide range of α-amino acids (differing only in the nature of the $R^3$ substituent) are known, and are commercially available. For the synthesis of Thiofoxins, Dimethylthiofoxins and Azafoxins the α-amino acids are readily reduced to yield β-amino alcohols (using protecting groups to retain the structure of the $R^3$ moiety if required). The diverse β-amino alcohols are then coupled to cysteine to yield "Thiofoxamines", to penicillamine to yield "Dimethylthiofoxamines", or to 3-aminoalanine to yield "Azafoxamines. These α-aminolactams can then be coupled to an appropriate acyl side chain by conventional amide coupling reactions (again protecting the $R^3$ substituent if required), yielding Thiofoxins, Dimethylthiofoxins or Azafoxins respectively.

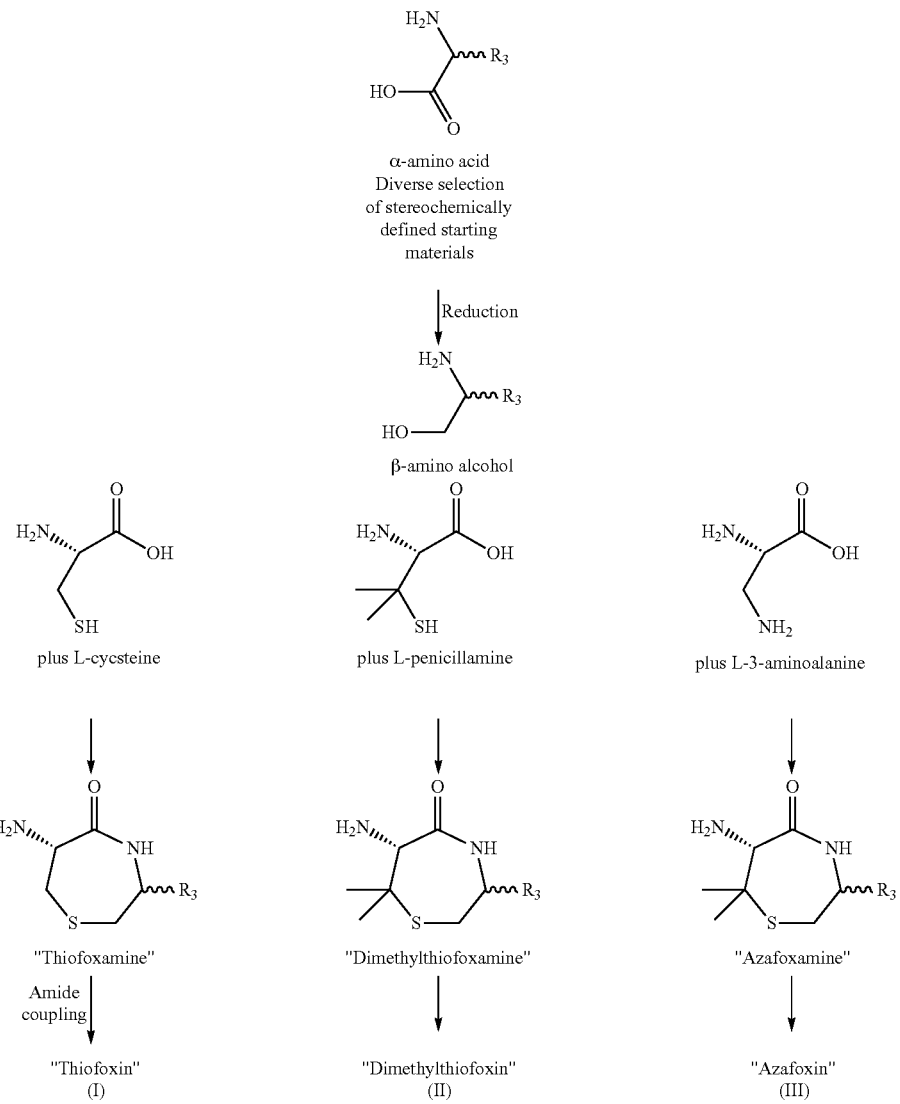

from widely available starting materials. Thiofoxins, Dimethylthiofoxins, Azafoxins and Amidofoxins each represent a diverse class of compounds (with diversity at the Z, $R^2$ (if applicable), $R^3$ and (if applicable) $R^4$ positions) which can be In contrast, Amidofoxins are generated by reacting the α-amino-acid (without first reducing it to the β-aminoalcohol) with 3-aminoalanine. It will be noticed that Amidofoxins are 7-membered ring analogs of the well-studied diketopiperazines generated from α-amino acid dimers, but generated from a dimer of a β-amino acid (3-aminoalanine) and an α-amino acid.

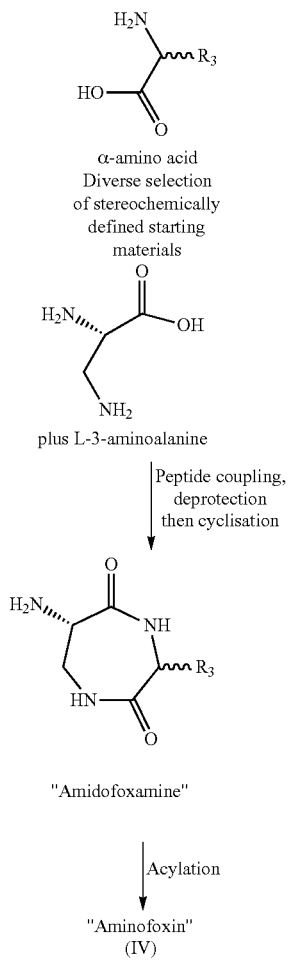

The resulting Thiofoxins, Dimethylthiofoxins, Azafoxins and Amidofoxins have the same range of R³ substituents as the original collection of available α-amino acids. Furthermore, general synthetic routes for generating α-amino acids are well known in the art (for example, see R. M. Williams, Synthesis of Optically Active a-Amino Acids (Pergamon, New York) 1989), allowing even greater diversity to be generated as required.

Alternatively or additionally, use of directly available β-amino alcohols, such as ephidrine, with variable 2-substitution allow the introduction of additional diversity as a variable R⁴ group at the 2-position of the ring in Thiofoxins, Dimethylthiofoxins and Azafoxins.

Alternatively or additionally, a prior reductive alkylation of the 3-aminoalanine moiety allows introduction of diversity at the N1 position in Azafoxins or Amidofoxins (the variable R² group).

A particular feature of the present invention is the facile stereocontrol of the synthesis. The exemplified routes use cheap and readily available L-cysteine, L-penicillamine and L-3-aminoalanine to couple with diverse β-amino alcohols (or directly with α-amino acids in the case of Amidofoxins). This results in a diverse series of α-aminolactams which are of the (S)-configuration. Alternatively, D-cysteine, D-penicil-lamine and D-3-aminoalanine are also readily available, and can be coupled with the same diverse β-amino alcohols (or α-amino acids) to yield α-aminolactams of the (R)-configuration. In the same way, by selecting the appropriate enantiomerically pure α-amino acid starting material, and then using a synthetic route which retains stereochemistry (such as the routes exemplified below), then Thiofoxamines, Dimethylthiofoxamines, Azafoxamines and/or Amidofoxamines and therefore Thiofoxins, Dimethylthiofoxins, Azafoxins and/or Amidofoxins with the appropriate configuration at the carbon bearing the R³-substituent can readily be synthesised. For example, performing the Thiofoxin synthesis with L-alanine and L-cysteine yields (6R)-amino-(3S)-methyl-[1,4]thiazapan-5-one. In contrast, performing the synthesis with D-alanine and L-cysteine yields (R,R)-6-amino-3-methyl-[1,4]thiazapan-5-one, using L-alanine and D-cysteine yields (S,S)-6-amino-3-methyl-[1,4]thiazapan-5-one, and using D-alanaine and D-cysteine yields (6S)-amino-(3R)-methyl-[1,4]thiazapan-5-one. Alternatively, racemic mixtures of one or both starting materials may be selected, yielding mixed stereoisomers of the Thiofoxamine, Dimethylthiofoxamine, Azafoxamine and/or Amidofoxamine and hence Thiofoxin, Dimethylthiofoxin, Azafoxin, and/or Amidofoxin products.

Importantly, it is possible to carry out the steps of the synthetic reactions in different orders as required. When generating a diverse library through combinatorial synthesis, it is important to generate as much of the diversity as possible late in the synthesis. Ideally, the last step should introduce the greatest diversity into the library. Since diversity may be introduced at several steps in the synthesis of the compounds of the invention (with variable Z, R² (for Azafoxins and Amidofoxins). R³ and R⁴ (for Thiofoxins, Dimethylthiofoxins and Azafoxins), it is possible to introduce diversity equally at each step (for example to have 8 different Z groups, R² groups and R³ groups in an Amidofoxin library, thereby yielding 512 compounds) or to introduce greater diversity at one of the steps (for example to have 2 different Z and R² groups, but 128 different R³ groups in an Amidofoxin library, thereby yielding 512 compounds). In such cases where diversity is introduced to a greater extent in one particular step it is advantageous to have this step as late as possible in the synthetic route. One advantage of the invention provided here is that the synthetic routes are well suited to changes in the order of the reaction steps. Specific examples of synthetic routes to yield Thiofoxins, Dimethylthiofoxins, Azafoxins, and Amidofoxins are provided in the examples below. For each of the classes, examples are given where the reaction steps are performed in different orders. However, It should be stressed that other synthetic routes exist which could alternatively be used, and would fall under the scope of the present invention.

It is envisaged that synthesis of library elements may be carried out using parallel synthesis methods well known in the art. For example, the synthesis may be performed using resins or other solid-phase supports to simplify the introduction of diversity and to facilitate the purification, or partial purification, of the library element products. Application of such solid phase, or other parallel synthesis, methodologies, whether manual, semi-automated or automated, to generate a library of Thiofoxins, Dimethylthiofoxins, Azafoxins or Amidofoxins falls under the scope of the present invention.

The invention also provides pharmaceutical compositions comprising, as active ingredient, a compound of general formula (I), (II), (III) or (IV), or a pharmaceutically acceptable salt thereof, and at least one pharmaceutically acceptable excipient and/or carrier.

By pharmaceutically acceptable salt is meant in particular the addition salts of inorganic acids such as hydrochloride, hydrobromide, hydroiodide, sulphate, phosphate, diphosphate and nitrate or of organic acids such as acetate, maleate, fumarate, tartrate, succinate, citrate, lactate, methanesulphonate, p-toluenesulphonate, palmoate and stearate. Also within the scope of the present invention, when they can be used, are the salts formed from bases such as sodium or potassium hydroxide. For other examples of pharmaceutically acceptable salts, reference can be made to "Salt selection for basic drugs", *Int. J. Pharm.* (1986), 33, 201-217.

The pharmaceutical composition can be in the form of a solid, for example powders, granules, tablets, gelatin capsules, liposomes or suppositories. Appropriate solid supports can be, for example, calcium phosphate, magnesium stearate, talc, sugars, lactose, dextrin, starch, gelatin, cellulose, methyl cellulose, sodium carboxymethyl cellulose, polyvinylpyrrolidine and wax. Other appropriate pharmaceutically acceptable excipients and/or carriers will be known to those skilled in the art.

The pharmaceutical compositions according to the invention can also be presented in liquid form, for example, solutions, emulsions, suspensions or syrups. Appropriate liquid supports can be, for example, water, organic solvents such as glycerol or glycols, as well as their mixtures, in varying proportions, in water.

The invention may also provide the use of a compound of general formula (I), (II), (III) and/or (IV), or a pharmaceutically acceptable salt thereof, for the preparation of a medicament intended to modulate the activity of one or more members of the G-protein coupled receptor (GPCR) class.

The invention provides compounds, compositions and uses of the compounds of general formula (I), (II), (III) and (IV) or their pharmaceutically acceptable salts, wherein the $R^1$ radical has a "key" carbon which is di-substituted with the same or different groups selected from: alkyl, haloalkyl, alkoxy, haloalkoxy, alkenyl, alkynl and alkylamino radicals.

The invention provides compounds, compositions and uses wherein the "key" carbon is chiral.

The invention provides compounds, compositions and uses wherein the "key" carbon has sp3 hybridised bonds.

The invention provides compounds, compositions and uses wherein the "key" carbon has essentially tetrahedral bond angles.

The compounds of general formula (I), (II), (III) or (IV) when used in the invention, or their salts, may be such that the ring or rings of Y constrain the bond angles at the "key" carbon to be essentially tetrahedral (i.e. sp3 hybrid bonds).

The invention also provides the sulfonamide analogues of the exemplified compounds: i.e. the sulfonyl-α-aminolactam-derived Thiofoxin, Dimethylthiofoxin, Azafoxin or Amidofoxin equivalents of the compounds of Formula (I), (II), (III) and (IV) respectively.

The invention includes compounds, compositions and uses thereof as defined, wherein the compound is in hydrated or solvated form.

The amide and sulfonamide Thiofoxins, Dimethylthiofoxins, Azafoxins and Amidofoxins described here are likely to be functional GPCR agonists and antagonists. The core consisting of the "key" carbon, the carbonyl or sulfonyl group, the α-amino group and the Thiofoxin, Dimethylthiofoxin, Azafoxin or Amidofoxin ring represents an example of a GPCR ligand. By varying the substitution of this core, particularly at the position bearing the $R^3$ substituent, it is possible to generate GPCR agonists and antagonists with a wide range of desirable properties much more readily than by screening random compound libraries.

As a result, the invention also provides for a library consisting of two or more members of the class of compounds designated by general formula (I), (II), (III) and/or (IV), such that the library may be screened to identify a molecule with a particular desirable set of properties with regard to modulating signalling at one (or more) GCPRs. The said library would then be screened for antagonist or agonist activity at the said GPCR(s) using methods well known in the art. For example, the library may be screened for the ability of individual library elements to block the binding of a radiolabelled GPCR ligand to a membrane preparation containing recombinant or purified GPCR. Alternatively, the library may be screened for the ability of individual library elements to stimulate cAMP production in cells expressing a recombinant GPCR.

Any Thiofoxin, Dimethylthiofoxin, Azafoxin or Amidofoxin compound according to the invention which exhibits desirable properties can be used as a template for synthesis of the analogous "Carbofoxin" (which has a carbon group rather than sulfur at the 1 position in Thiofoxins or Dimethylthiofoxins, or nitrogen at the 1 position in Azafoxins or Amidofoxins), for example by using ring-closing metathesis synthetic routes which are well known in the art (such as Truka, T. M.; Grubbs, R. H. Acc. Chem. Res. 2001, 34, 18). Suitable ring closing-metathesis routes have also been exemplified which could be used to synthesise "Carbofoxin" analogs of Azafoxins or Amidofoxins where the N at position 1 is substituted (i.e. $R^2 \neq H$), such as the method of Del Valle R. R. and Goodman M., J. Org. Chem. 2004, 69. 8946. Such "Carbofoxin" compounds are expected to be useful GPCR agonists or antagonists.

The invention also provides a method of treatment, amelioration or prophylaxis of the symptoms of disease or condition selected from the group consisting of hypertension, atherosclerosis, asthma, obesity, neurodegenerative disorders, autoimmune disorders or psychopathic disorders by the administration to a patient of an effective amount of a compound, composition or medicament of the invention designed to modulate GPCR activity.

DEFINITIONS

The term "about" refers to an interval around the considered value. As used in this patent application, "about X" means an interval from X minus 10% of X to X plus 10% of X, and preferably an interval from X minus 5% of X to X plus 5% of X.

The use of a numerical range in this description is intended unambiguously to include within the scope of the invention all individual integers within the range and all the combinations of upper and lower limit numbers within the broadest scope of the given range. Hence, for example, the range of 1 to 20 carbon atoms specified in respect of (inter alia) formula I is intended to include all integers between 1 and 20 and all sub-ranges of each combination of upper and lower numbers, whether exemplified explicitly or not.

As used herein, the term "comprising" is to be read as meaning both comprising and consisting of: Consequently, where the invention relates to a "pharmaceutical composition comprising as active ingredient" a compound, this terminology is intended to cover both compositions in which other active ingredients may be present and also compositions which consist only of one active ingredient as defined.

The term "peptidic moieties" used herein is intended to include the following 20 naturally-occurring proteogenic amino acid residues:

| SYMBOL | MEANING |
|---|---|
| Ala | Alanine |
| Cys | Cysteine |
| Asp | Aspartic Acid |
| Glu | Glutamic Acid |
| Phe | Phenylalanine |
| Gly | Glycine |
| His | Histidine |
| Ile | Isoleucine |
| Lys | Lysine |
| Leu | Leucine |
| Met | Methionine |
| Asn | Asparagine |
| Pro | Proline |
| Gln | Glutamine |
| Arg | Arginine |
| Ser | Serine |
| Thr | Threonine |
| Val | Valine |
| Trp | Tryptophan |
| Tyr | Tyrosine |

Modified and unusual amino acid residues, as well as peptido-mimetics, are also intended to be encompassed within the definition of "peptidic moieties".

Unless otherwise defined, all the technical and scientific terms used here have the same meaning as that usually understood by an ordinary specialist in the field to which this invention belongs. Similarly, all the publications, patent applications, all the patents and all other references mentioned here are incorporated by way of reference (where legally permissible).

The following examples are presented in order to illustrate the invention and should in no way be considered to limit the scope of the invention.

EXAMPLES

In each of the following examples, a range of protecting groups are used. The functional properties of the required protecting groups are specified (that is, in certain steps it is required that two different protecting groups are used which are removed by different reaction conditions—i.e. orthogonal protecting groups), but the molecular composition is not specified. Any suitable protecting group well known in the art may be substituted. Consequently, variable elements of such protecting groups are designated $R^5$, $R^6$, $R^7$ and/or $R^8$ in the following examples. The protecting groups (and hence the $R^5$, $R^6$, $R^7$ and $R^8$ substituents) are not themselves part of the products falling under the scope of the invention.

Example 1

Synthesis of Thiofoxins

The Thiofoxins are products of the coupling of cysteine with a β-amino alcohol (possibly derived from the reduction of an α-amino acid). In the first scheme (Scheme 1A below), the $R^1$ group is introduced, then the $R^3/R^4$ group, and then the compounds are cyclised. Such a route would be optimal if greater diversity was to be introduced at $R^3/R^4$ than $R^1$.

Scheme 1A

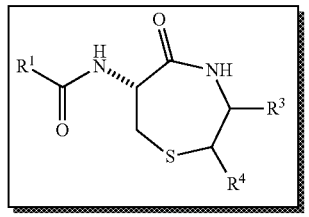

6-Acylamino-[1,4]thiazepan-5-ones

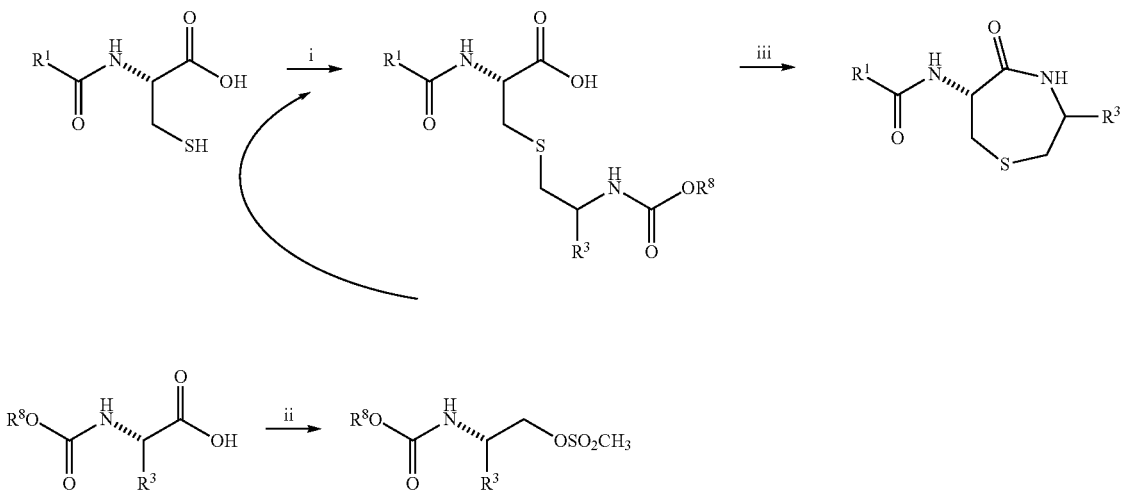

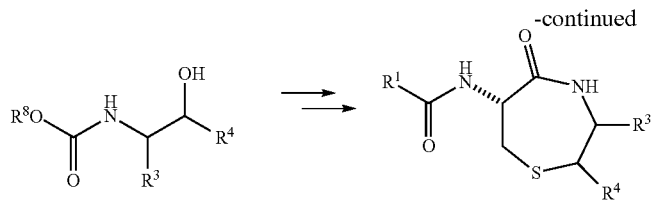

Other amino alcohols, such as norephedrine, could be used to introduce further substituents.

Introducing R¹, then R³/R⁴, the cyclisation:
Reagents and Conditions:
i, alkylation of S, e.g. J. Med. Chem. 1987, 30, 1984-1991
ii, Reduction then mesylation of protected amino acids, e.g. Synthesis 1992, 1359 and Synthesis 1996, 1223
iii, ring closure with peptide coupling reagent, e.g. J. Med. Chem, 1987, 30, 1984-1991

In the first step the $R^1$-containing acyl (or sulfonamide) substituent is introduced by an appropriate amide coupling route, several of which are well known in the art, e.g. DCC coupling.

Separately, one or more β-amino alcohols are obtained (e.g. ephedrine) or synthesised from α-amino acids, In each case, the amino group is protected (e.g. by addition of a Boc group, or by obtaining the appropriately protected α-amino acid from a commercial supplier). Boc-protected amino acids are converted to amino alcohols by reduction, and the Boc-protected β-amino alcohol (whether purchased or obtained by reduction of an amino acid) is modified so as to provide a suitable leaving group to allow alkylation of the side-chain heteroatom (in this case, the sulfur of cysteine), for example the amino-protected β-amino alcohol could be mesylated. Several suitable methods for reduction and mesylation exist, and are well known in the art (e.g. Synthesis (1992) 1359 or Synthesis (1996) 1223).

In the next step, the acylcysteine is alkylated at the sulfur centre using any of several appropriate methods which are well known in the art (e.g. J Med. Chem. (1987) 30:1984). Each β-amino alcohol is reacted separated with an appropriate acylcysteine to yield individual library elements with variable $R^1$, $R^2$ and $R^3$ depending on the selection of acylcysteines and β-amino alcohols available. The nitrogen introduced at this step is hereafter termed the ω-amine group.

In the final step, the S-alkyl acylcysteines are cyclised. The ω-amine is selectively deprotected and condensed with the carboxy ester (or after selective hydrolysis the corresponding carboxylic acid) to form a seven-membered ring, yielding Thiofoxin library elements. Similar methods are well known in the art (e.g. J. Med. Chem. (1987) 30:1984).

In the second scheme (Scheme 1B below), the $R^3/R^4$ groups are introduced, then the compounds are cyclised and finally the $R^1$ group is introduced. Such a route would be optimal if greater diversity was to be introduced at $R^1$ than $R^3/R^4$ Scheme 1B

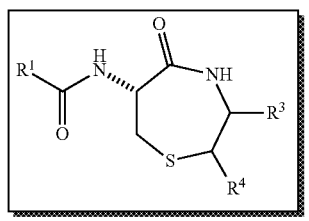

6-Acylamino-[1,4]thiazepan-5-ones

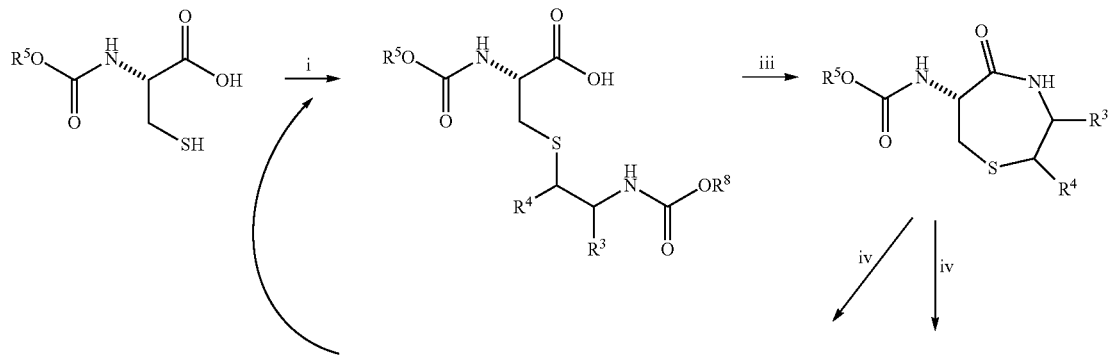

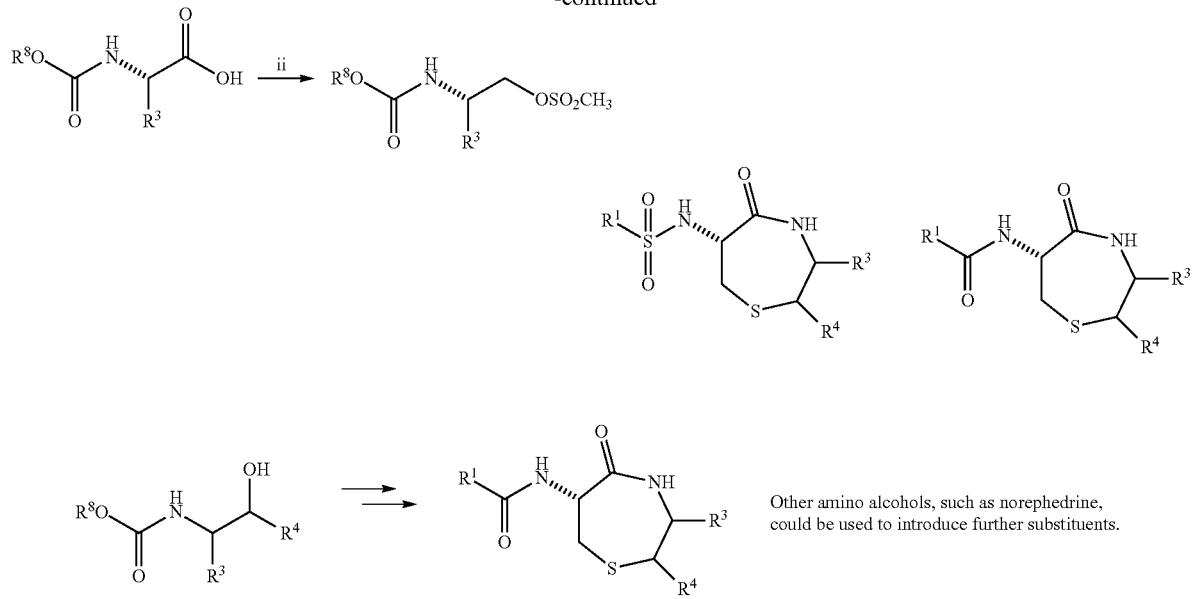

Introducing $R^3/R^4$, then cyclisation, then $R^1$
Reagents and Conditions:
i, alkylation of S, e.g. J. Med. Chem. 1987, 30, 1984-1991
ii, Reduction then mesylation of protected amino acids, e.g.
Synthesis 1992, 1359 and Synthesis 1996, 1223
iii, selective removal of $R^8OCO$ group (leaving $R^1OCO$ group intact) then ring closure with peptide coupling reagent, e.g. J. Med. Chem. 1987, 30, 1984-1991.
iv, removal of $R^5OCO$ group and subsequent acylation of free amino group with activated $R^1CO_2H$ or activated $R^1SO_3H$ In the first step, cysteine is selectively protected at the α-amine, and is then alkylated on S with an N-protected β-amino-alcohol in which the alcohol has been activated to form a leaving group suitable for nucleophilic substitution with inversion of stereochemistry at carbon. The introduced nitrogen is here-on called the ω-amine group (for similar see Tetrahedron, 1999, 55, 10155).

One or more β-amino alcohols suitable for this alkylation are obtained (e.g. ephedrine) or synthesised from α-amino acids, In each case, the amino agroup is protected (e.g. by addition of a Boc group, or by obtaining the appropriately protected α-amino acid from a commercial supplier). Boc-protected amino acids are converted to amino alcohols by reduction, and the Boc-protected β-amino alcohol (whether purchased or obtained by reduction of an amino acid) is mesylated. Several suitable methods for reduction and mesylation exist, and are well known in the art (e.g. Synthesis (1992) 1359 or Synthesis (1996) 1223).

In the next step, the ω-amine is selectively deprotected and condensed with the carboxy ester (or after selective hydrolysis the corresponding carboxylic acid) to form a seven-membered ring (according to J. Med. Chem., 1987, 30, 1984).

In the final step, following cyclisation, the α-amine is selectively deprotected and acylated as required to introduce diversity at the $R^1$ position, using an appropriate peptide coupling reagent, several of which are well known in the art.

In the third scheme (Scheme 1C below), the $R^3/R^4$ groups are introduced, then the $R^1$ group, and finally the compounds are cyclised. Such a route might be useful if greater diversity was to be introduced at $R^1$ than $R^3/R^4$.

Scheme 1C

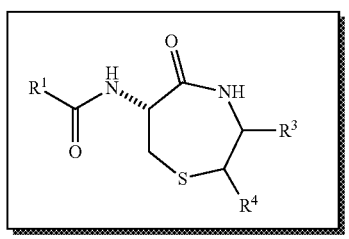

6-Acylamino-[1,4]thiazepan-5-ones

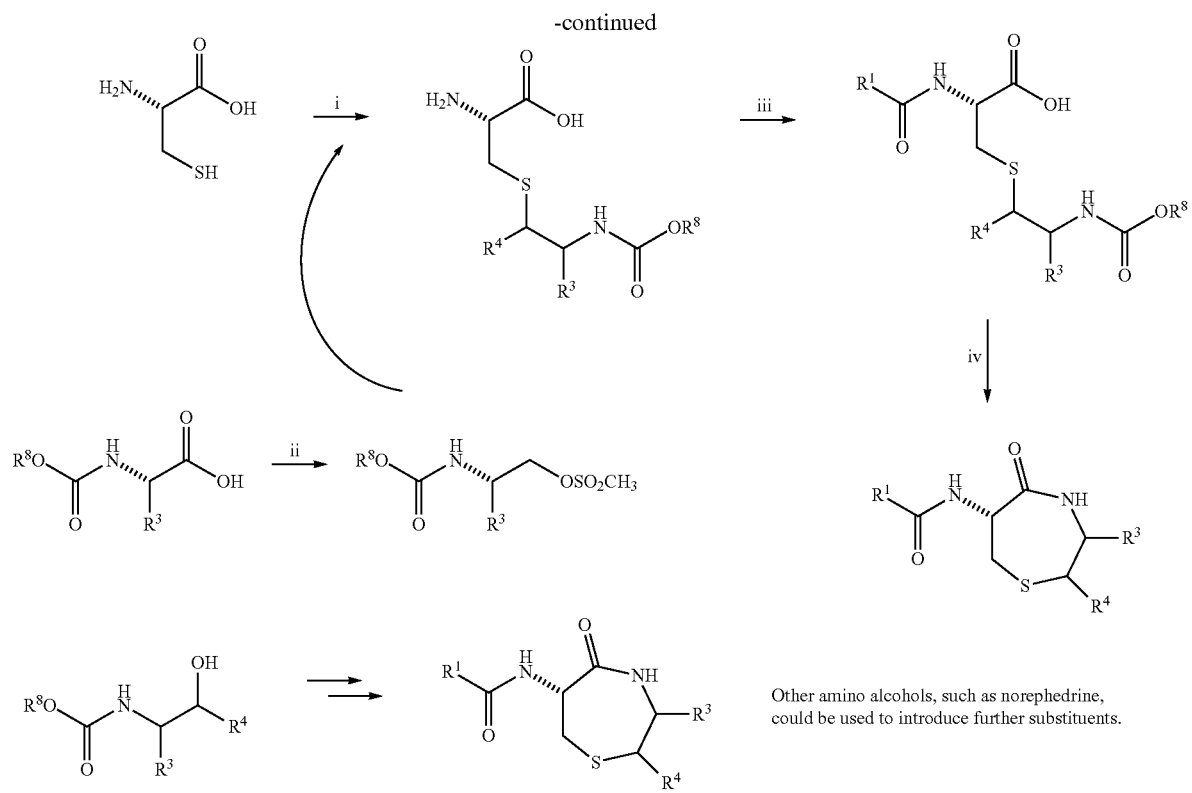

Introducing R³/R⁴, then R¹, then cyclisation,
Reagents and Conditions:
i, alkylation of S, e.g. J. Med. Chem. 1987, 30, 1984-1991
ii, Reduction then mesylation of protected amino acids, e.g.
Synthesis 1992, 1359 and Synthesis 1996, 1223
iii, acylation of free amino group with activated R¹CO₂H
iv, selective removal of R⁸OCO group then ring closure with
peptide coupling reagent, e.g. J. Med. Chem. 1987, 30, 1984-1991.

This route is similar to Scheme 1B, except that the acylation of the α-amine of cysteine is performed prior to the cyclisation (for similar see Tetrahedron, 1999, 55, 10155).

These three schemes illustrate the facile nature of the synthesis of a library composed of one or more Thiofoxin elements. In particular, the ability to perform the steps of the reaction in various orders in order to allow greater diversity to be introduced into different regions of the molecule while keeping the synthesis practicable is illustrated.

A number of related structures are already known in the literature, including two examples described as GPCR ligands.

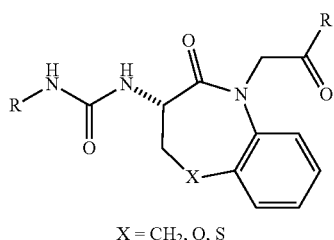
(V)

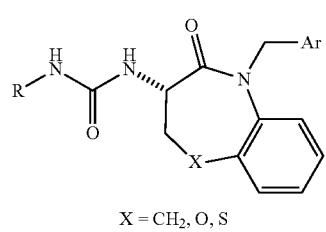
(VI)

Compound (V) is a histamine H2 or gastrin receptor ligand (depending on the nature of R and X) described in Bioorg. Med. Chem. (1997) 5:1411 and compound (VI) is a Neuropeptide Y receptor ligand described in Bioorg. Med. Chem., (1999) 7:1703. Although clearly related in structure to Thiofoxins, neither compound is a Thiofoxin, nor falls under the scope of the present invention because of the presence of substitution at the N4 position. However, the existence of these compounds underlines the high density of GPCR ligands likely to be found in libraries composed of, or enriched in, Thiofoxins.

Example 2

Synthesis of Dimethylthiofoxins

The Dimethylthiofoxins are analagous to the Thiofoxins, except that penicillamine is used in place of cysteine. Dimethylthiofoxins are then products of the coupling of penicillamine with a β-amino alcohol (possibly derived from the reduction of an α-amino acid). In the first scheme (Scheme 2A below), the $R^1$ group is introduced, then the $R^3/R^4$ group, and then the compounds are cyclised. Such a route would be optimal if greater diversity was to be introduced at $R^3/R^4$ than $R^1$.

group, or by obtaining the appropriately protected α-amino acid from a commercial supplier). Boc-protected amino acids are converted to amino alcohols by reduction, and the Boc-protected β-amino alcohol (whether purchased or obtained by reduction of an amino acid) is mesylated. Several suitable methods for reduction and mesylation exist, and are well known in the art (e.g. Synthesis (1992) 1359 or Synthesis (1996) 1223).

In the next step, the acylpenicillamine is alkylated at the sulfur centre using any of several appropriate methods which are well known in the art (e.g. J Med. Chem. (1987) 30:1984). Each β-amino alcohol is reacted separately with an appropriate acylpenicillamine to yield individual library elements Scheme 2A

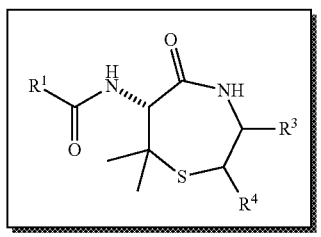

6-Acylamino-7,7-dimethyl[1,4]thiazepan-5-ones

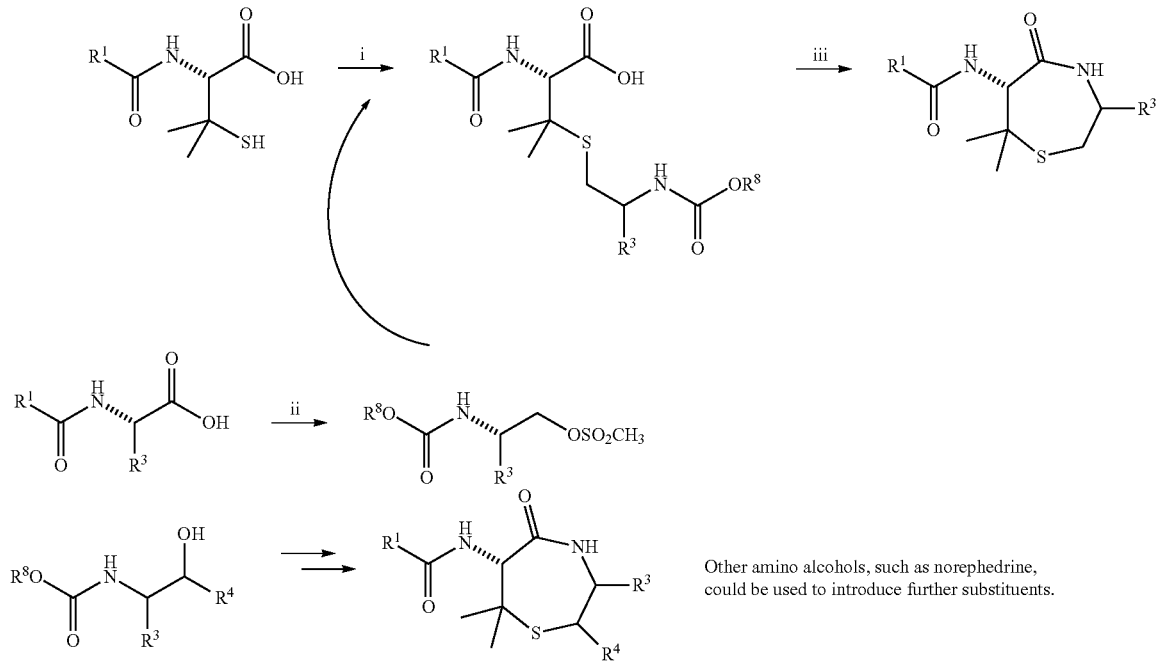

Other amino alcohols, such as norephedrine, could be used to introduce further substituents.

Introducing $R^1$, then $R^3/R^4$, the cyclisation:
Reagents and Conditions:
i, alkylation of S, e.g. J. Med. Chem. 1987, 30, 1984-1991
ii, Reduction then mesylation of protected amino acids, e.g.
Synthesis 1992, 1359 and Synthesis 1996, 1223
iii, ring closure with peptide coupling reagent, e.g. J. Med. Chem. 1987, 30, 1984-1991

In the first step the $R^1$-containing acyl (or sulfonamide) substituent is introduced onto pencillamine by an appropriate amide coupling route, several of which are well known in the art, e.g., DCC coupling.

Separately, one or more β-amino alcohols are obtained (e.g. ephedrine) or synthesised from α-amino acids. In each case, the amino agroup is protected (e.g. by addition of a Boc with variable $R^1$, $R^2$ and $R^3$ depending on the selection of acylcysteines and β-amino alcohols available. The nitrogen introduced at this step is hereafter termed the ω-nitrogen.

In the final step, the S-alkyl acylpencillamines are cyclised. The ω-amine is selectively deprotected and condensed with the carboxy ester (or after selective hydrolysis the corresponding carboxylic acid) to form a seven-membered ring, yielding Dimethylthiofoxin library elements. Similar methods are well known in the art (e.g. J. Med. Chem. (1987) 30:1984).

In the second scheme (Scheme 2B below), the $R^3/R^4$ groups are introduced, then the compounds are cyclised and finally the $R^1$ group is introduced. Such a route would be optimal if greater diversity was to be introduced at $R^1$ than $R^3/R^4$ In the first step, penicillamine is selectively protected at the α-amine, and is then alkylated on S with an N-protected β-amino-alcohol in which the alcohol has been activated to form a leaving group suitable for nucleophilic substitution with inversion of stereochemistry at carbon. The introduced nitrogen is here-on called the ω-amine group (for similar see Tetrahedron, 1999, 55, 10155).

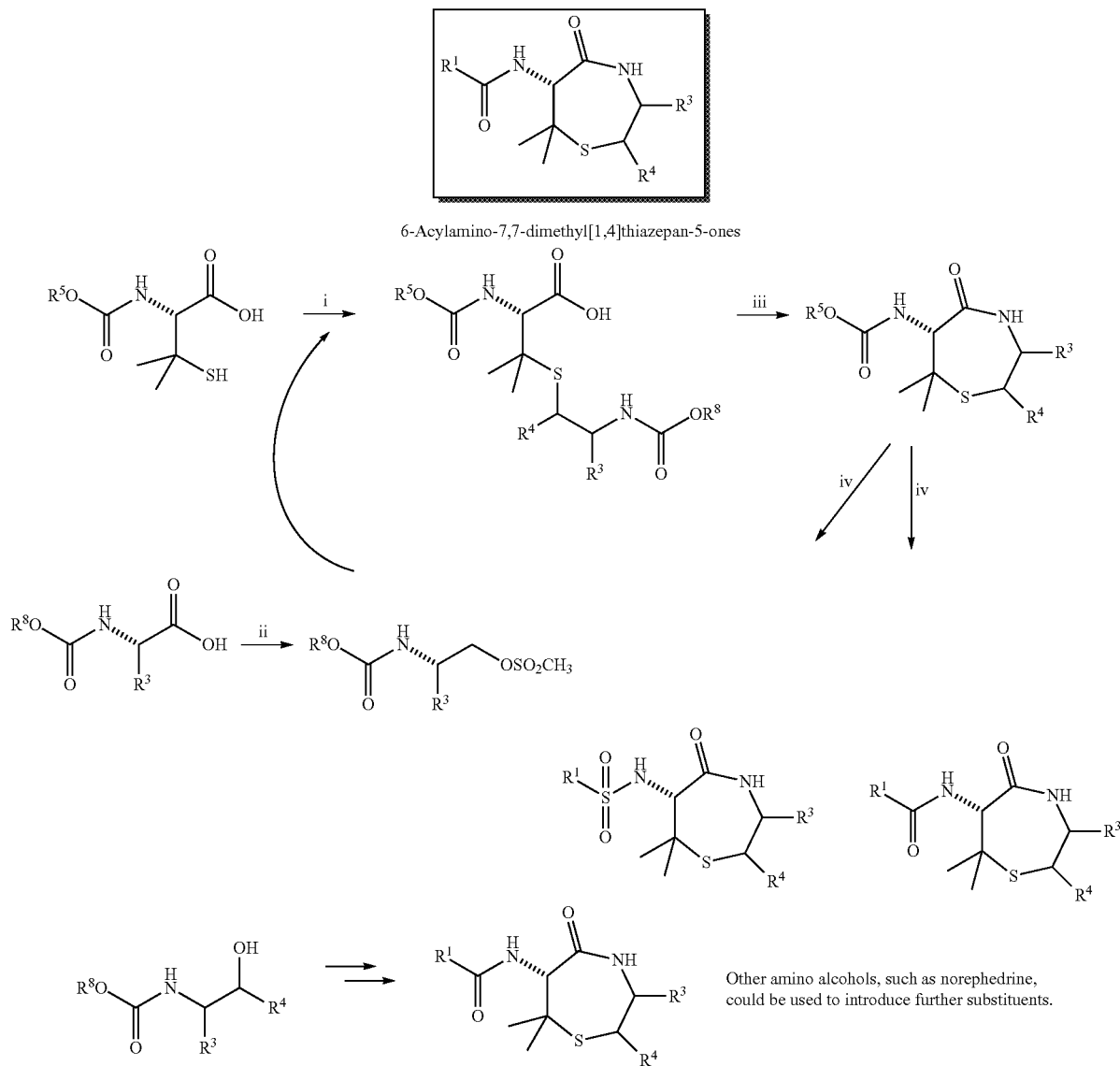

Introducing $R^3/R^4$, then cyclisation, then $R^1$
Reagents and Conditions:
i, alkylation of S, e.g. J. Med. Chem. 1987, 30, 1984-1991
ii, Reduction then mesylation of protected amino acids, e.g. Synthesis 1992, 1359 and Synthesis 1996, 1223
iii, selective removal of $R^8OCO$ group (leaving $R^1OCO$ group intact) then ring closure with peptide coupling reagent, e.g. J. Med. Chem. 1987, 30, 1984-1991.
iv, removal of $R^5OCO$ group and subsequent acylation of free amino group with activated $R^1CO_2H$ or activated $R^1SO_3H$ One or more β-amino alcohols suitable for this alkylation are obtained (e.g. ephedrine) or synthesised from α-amino acids, In each case, the amino agroup is protected (e.g. by addition of a Boc group, or by obtaining the appropriately protected α-amino acid from a commercial supplier). Boc-protected amino acids are converted to amino alcohols by reduction, and the Boc-protected β-amino alcohol (whether purchased or obtained by reduction of an amino acid) is mesylated. Several suitable methods for reduction and mesylation exist, and are well known in the art (e.g. Synthesis (1992) 1359 or Synthesis (1996) 1223).

In the next step, the ω-amine is selectively deprotected and condensed with the carboxy ester (or after selective hydrolysis the corresponding carboxylic acid) to form a seven-membered ring (according to J. Med. Chem., 1987, 30, 1984).

In the final step, following cyclisation, the α-amine is selectively deprotected and acylated as required to introduce diversity at the $R^1$ position, using an appropriate peptide coupling reagent, several of which are well known in the art.

In the third scheme (Scheme 2C below), the $R^3/R^4$ groups are introduced, then the $R^1$ group, and finally the compounds are cyclised. Such a route might be useful if greater diversity was to be introduced at $R^1$ than $R^3/R^4$.

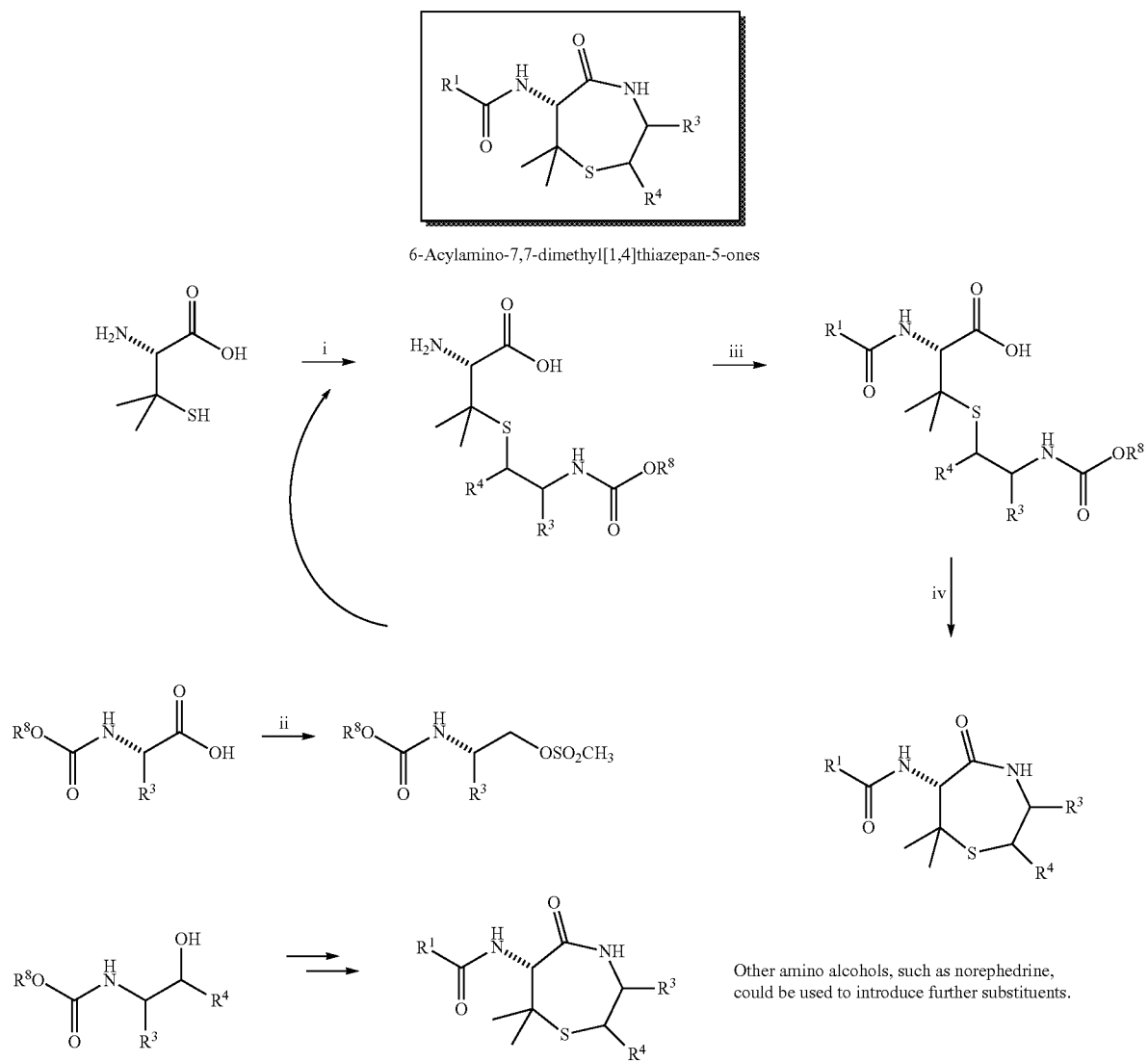

Other amino alcohols, such as norephedrine, could be used to introduce further substituents.

Introducing $R^3/R^4$, then $R^1$, then cyclisation,
Reagents and Conditions:
i, alkylation of S, e.g. J. Med. Chem. 1987, 30, 1984-1991
ii, Reduction then mesylation of protected amino acids, e.g. Synthesis 1992, 1359 and Synthesis 1996, 1223
iii, acylation of free amino group with activated $R^1CO_2H$
iv, selective removal of $R^8OCO$ group then ring closure with peptide coupling reagent, e.g. J. Med. Chem. 1987, 30, 1984-1991.

This route is similar to Scheme 2B, except that the acylation of the α-amine of penicillamine is performed prior to the cyclisation (for similar see Tetrahedron, 1999, 55, 10155).

These three schemes illustrate the facile nature of the synthesis of a library composed of one or more Dimethylthiofoxin elements. In particular, the ability to perform the steps of the reaction in various orders in order to allow greater diversity to be introduced into different regions of the molecule while keeping the synthesis practicable is illustrated.

Many compounds related in structure to the Dimethylthioxoins are known in the public domain (see for example J. Chem. Soc., Chem. Commum., 1993, 1599 and Liebigs Ann. Recl. 1997, 1711), because cyclisation products between penicillamine and other α-amino acids are analogs or biosynthetic intermediates of well-studied β-lactam antibiotics such as penicillin. However, these penicillin analogs have carboxylate or the ester, thioester or amide derivative of carboxylate as the substituent at the 3-position of the ring.

Example 3

Synthesis of Azafoxins

The Azafoxins are the products of the coupling of 3-aminoalanine with a β-amino alcohol (possibly derived from the reduction of an α-amino acid). Unlike the sulfur-containing lactams (Thiofoxins and Dimethylthiofoxins), the introduction of a further nitrogen into the lactam ring in Azafoxins allows for the possibility of further substitution (and hence diversity) at the ring heteroatom. In the first scheme (Scheme 3A below), the $R^1$ group is introduced, then the $R^2$ group (substitution at nitrogen) and then the $R^3/R^4$ group, before finally the compounds are cyclised. Such a route would be optimal if greater diversity was to be introduced at $R^3/R^4$ than $R^2$ with least diversity at $R^1$.

Scheme 3A

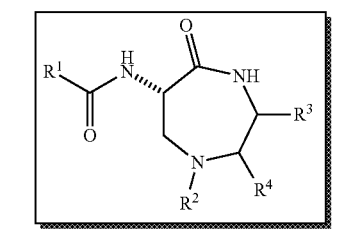

6-Acylamino-1-acyl/alkyl-1,4-diazepan-5-ones

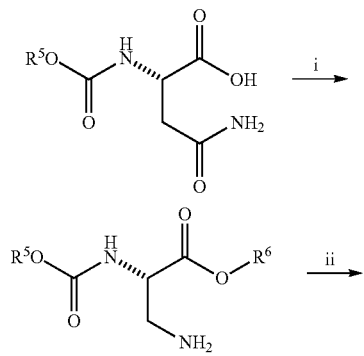

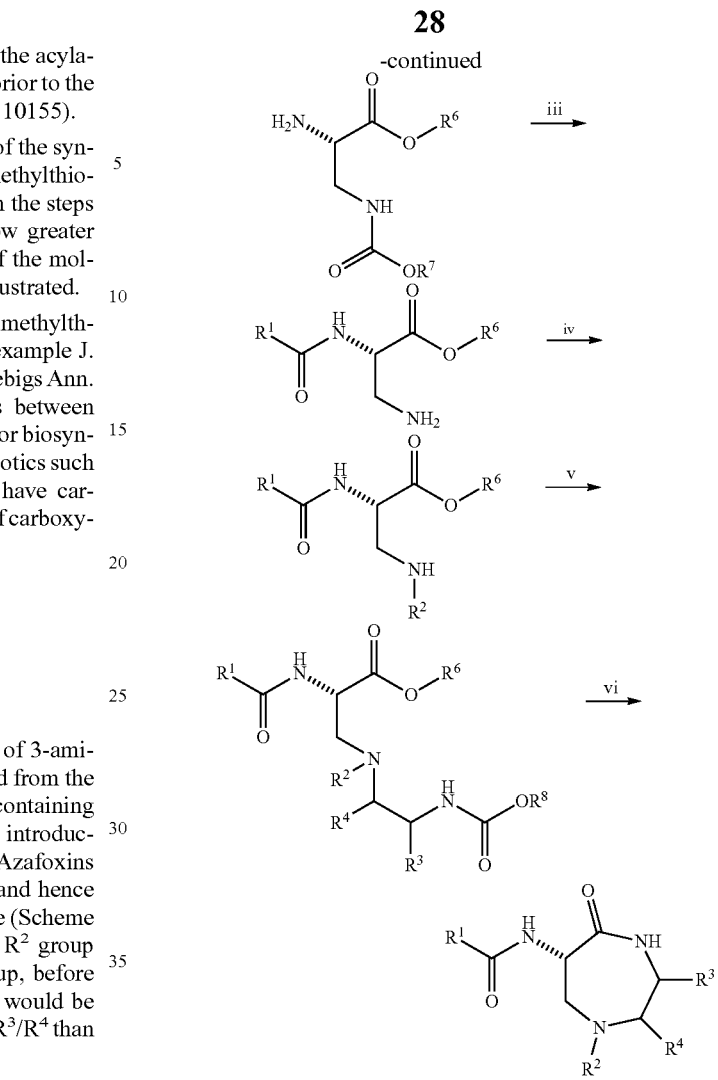

Introduction $R^1$, then $R^2$ then $R^3/R^4$
Reagents and Conditions
i) Hoffman degradation J. Org. Chem. 1997, 62, 6918, then ester formation.
ii) orthogonal protection of β-amine, then deprotection of α-amine by selective removal of $R^5$OCO group.
iii) acylation of α-amine, then selective deprotection of β-amine by removal of $R^7$OCO group.
iv) Functionalisation of β-amine via alkylation, arylation or reductive alkylation, or acylation with sulfonyl chloride.
v) Reductive amination of β-amine with protected amino aldehyde, see J. Org. Chem., 2002, 67, 4017 or alkylation with activated protected amino-alcohol.
vi) Selective deprotection and cyclisation in the style of J. Med. Chem. 1987, 30, 1984-1991.

In the first step, a protected 3-aminoalanine is synthesised, for example by the Hoffman degradation of N-α-carbamate ester protected asparagine (according to J. Org. Chem., 1997, 62, 6918), and the carboxyllic acid is esterified ((according to J. Med. Chem., 1998, 41, 2786).

In order to introduce substitution at the α-amine, the free β-amine is then orthogonally protected and the α-amine selectively deprotected by removal of the carbamate ester. The free α-amine is then acylated as in the previous examples to introduce the $R^1$ functionality.

Next, the $R^2$ functionality is introduced, for example by mono-alkylation, mono-arylation or reductive alkylation, or by acylation with sulfonyl chloride, using reaction conditions well known in the literature.

The β-amine is then alkylated with an N-protected β-amino-alcohol in which the alcohol has been activated to form a leaving group suitable for nucleophilic substitution with inversion of stereochemistry at carbon (as described for Thiofoxins and Dimethylthiofoxins). Alternatively the β-amine can be condensed with an N-protected α-amino-aldehyde in the presence of a reducing agent forming an amine (according to J. Org. Chem., 2002, 67, 4017). The introduced nitrogen is here-on called the ω-amine group. This step introduces the $R^3/R^4$ functionality, depending on the selected β-aminoalcohol (possibly derived from an α-amino acid).

In the final step (as for Thiofoxins and Dimethylthiofoxins), the ω-amine is selectively deprotected and condensed with the carboxy ester (or after selective hydrolysis the corresponding carboxylic acid) to form a seven-membered ring (according to J. Med. Chem., 1987, 30, 1984).

In the second scheme (Scheme 3B below), the $R^1$ group is introduced, then the $R^3/R^4$ group(s) are introduced and the compounds are cyclised, and then finally the $R^2$ group (substitution at nitrogen) is introduced. Such a route would be optimal if greater diversity was to be introduced at $R^2$ than $R^3/R^4$ with least diversity at $R^1$.

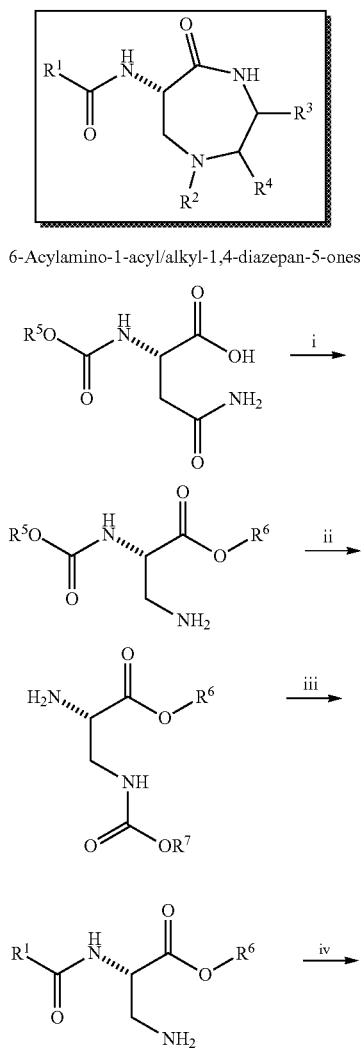

Scheme 3B

6-Acylamino-1-acyl/alkyl-1,4-diazepan-5-ones

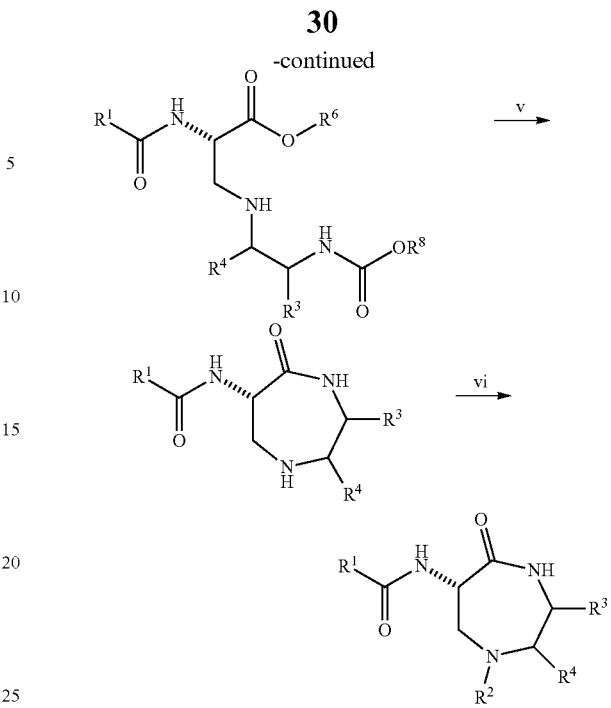

Introducing $R^1$ then $R^3/R^4$ then $R^2$
Reagents and conditions
i) Hoffman degradation J. Org. Chem. 1997, 62, 6918, then ester formation.
ii) orthogonal protection of β-amine, then deprotection of α-amine by selective removal of $R^5OCO$ group.
iii) acylation of α-amine, then selective deprotection of β-amine by removal of $R^7OCO$ group.
iv) Reductive amination of β-amine with protected amino aldehyde, see J. Org. Chem., 2002, 67, 4017 or alkylation with activated protected amino-alcohol.
v) Selective deprotection and cyclisation in the style of J. Med. Chem. 1987, 30, 1984-1991.
vi) Functionalisation of β-amine via alkylation, arylation or reductive alkylation, or acylation with acid chloride, isocyanate, chloroformate, chloroformamide, sulfonyl chloride, activated acid, amino acid, or peptide.

In this scheme, protected 3-aminoalanine is synthesised, for example by Hoffman degradation of N-α-protected asparagine, and is then orthogonally protected on the β-amine, deprotected and acylated at the α-amine and esterified at the carboxylic acid all as described for Scheme 3A.

Then, following selective deprotection of the β-amine, it is alkylated on nitrogen with an N-protected β-amino-alcohol in which the alcohol has been activated to form a leaving group suitable for nucleophilic substitution with inversion of stereochemistry at carbon (as described for Thiofoxins and Dimethylthiofoxins). Alternatively the β-amine can be condensed with an N-protected α-amino-aldehyde in the presence of a reducing agent forming an amine (according to J. Org. Chem., 2002, 67, 4017). The introduced nitrogen is here-on called the ω-amine group. This step introduces the $R^3/R^4$ functionality, depending on the selected β-aminoalcohol (possibly derived from an α-amino acid).

The ω-amine is then selectively deprotected and condensed with the carboxy ester (or after selective hydrolysis the corresponding carboxylic acid) to form a seven-membered ring (according to J. Med. Chem., 1987, 30, 1984).

Finally, the $R^2$ functionality is introduced, for example by mono-alkylation, mono-arylation or reductive alkylation, or by acylation with sulfonyl chloride, using reaction conditions well known in the literature.

In the third scheme (Scheme 3C below), the $R^2$ group is introduced, then the $R^1$ group and then the $R^3/R^4$ group(s), before the compounds are finally cyclised. Such a route would be optimal if greater diversity was to be introduced at $R^3/R^4$ than $R^1$ with least diversity at $R^2$.

Scheme 3C

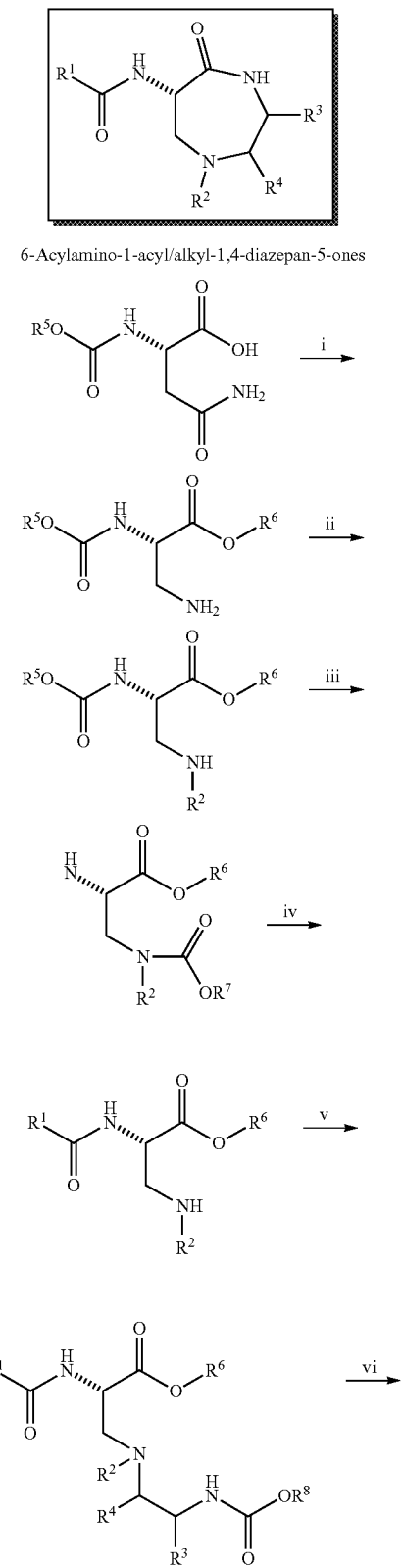

6-Acylamino-1-acyl/alkyl-1,4-diazepan-5-ones

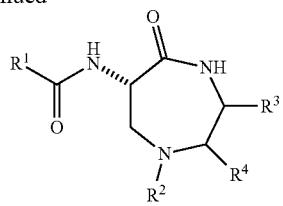

Introducing $R^2$ then $R^1$ then $R^3/R^4$
Reagents and conditions
i) Hoffman degradation J. Org. Chem. 1997, 62 6918, then ester formation.
ii) Functionalisation of β-amine via alkylation, arylation or reductive alkylation, or acylation with sulfonyl chloride.
iii) orthogonal protection of β-amine (if necessary), then deprotection of α-amine by selective removal of $R^5OCO$ group.
iv) acylation of α-amine, then selective deprotection of β-amine by removal of $R^7OCO$ group.
v) Reductive amination of β-amine with protected amino aldehyde, see J. Org. Chem., 2002, 67, 4017 or alkylation with activated protected amino-alcohol.
vi) Selective deprotection and cyclisation in the style of J. Med. Chem. 1987, 30, 1984-1991.

In this scheme, protected 3-aminoalanine is synthesised, for example by Hoffman degradation of N-α-protected asparagine, and the carboxylic acid esterified (as in Scheme 3A, for example), but the β-amine is then mono-alkylated, mono-arylated or sulfonated as required to introduce the $R^2$ functionality, using methods well known in the literature. Thereafter, the secondary β-amine is protected orthogonally to the α-amine.

In the next step, the α-amine is selectively deprotected and acylated as described above to introduce the $R^1$ functionality.

Then, following deprotection of the β-amine, it is alkylated on nitrogen with an N-protected β-amino-alcohol in which the alcohol has been activated to form a leaving group suitable for nucleophilic substitution with inversion of stereochemistry at carbon (as described for Thiofoxins and Dimethylthiofoxins). Alternatively the β-amine can be condensed with an N-protected α-amino-aldehyde in the presence of a reducing agent forming an amine (according to J. Org. Chem., 2002, 67, 4017). The introduced nitrogen is here-on called the ω-amine group. This step introduces the $R^3/R^4$ functionality, depending on the selected β-aminoalcohol (possibly derived from an α-amino acid).

The ω-amine is then selectively deprotected and condensed with the carboxy ester (or after selective hydrolysis the corresponding carboxylic acid) to form a seven-membered ring (according to J. Med. Chem., 1987, 30, 1984).

In the fourth scheme (Scheme 3D below), the $R^2$ group is introduced, then the $R^3/R^4$ group(s). The compounds are next cyclised, and finally the $R^1$ group is introduced. Such a route would be optimal if greater diversity was to be introduced at $R^1$ than $R^3/R^4$ with least diversity at $R^2$.

Scheme 3D

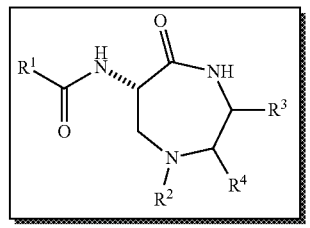

6-Acylamino-1-acyl/alkyl-1,4-diazepan-5-ones

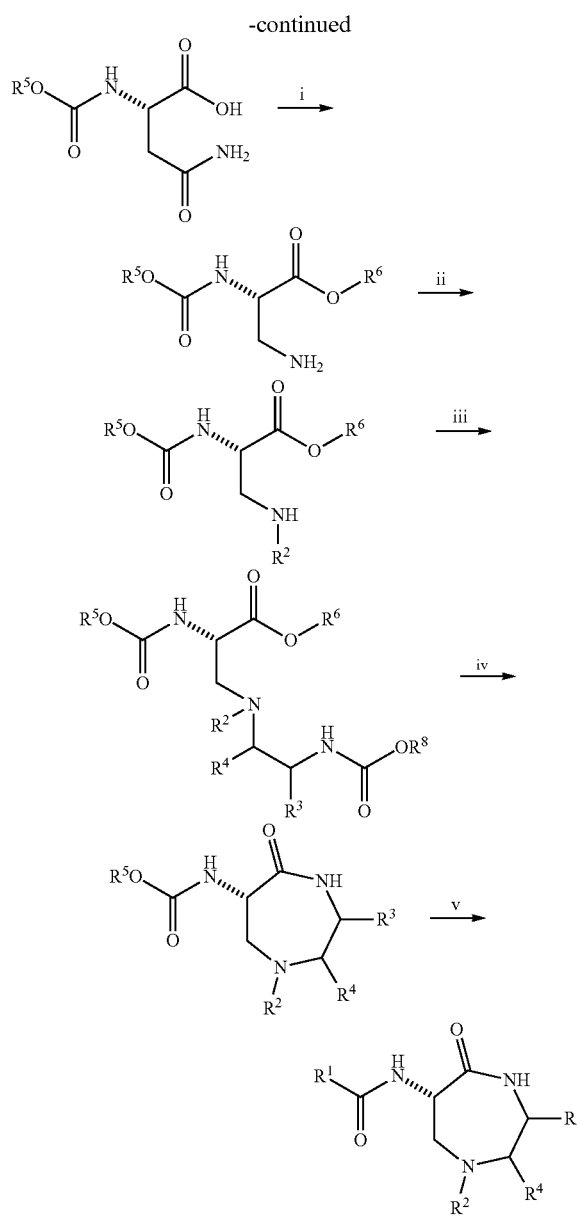

Introducing R² then R³/R⁴ then R¹
Reagents and conditions
i) Hoffman degradation J. Org. Chem. 1997, 62 6918, then ester formation.
ii) Functionalisation of β-amine via alkylation, arylation or reductive alkylation, or acylation with sulfonyl chloride.
iii) Reductive amination of β-amine with protected amino aldehyde, see J. Org. Chem., 2002, 67, 4017 or alkylation with activated protected amino-alcohol.
vi) Selective deprotection and cyclisation in the style of J. Med. Chem. 1987, 30, 1984-1991.
v) deprotection of α-amine by selective removal of R⁵OCO group and acylation of α-amine In this scheme, protected 3-aminoalanine is synthesised, for example by Hoffman degradation of N-α-protected asparagine, and the carboxylic acid esterified. The β-amine is then mono-alkylated, mono-arylated or sulfonated as required to introduce the R² functionality, using methods well known in the literature, all as in Scheme 3C.

In the next step, the secondary β-amine, is alkylated on nitrogen with an N-protected β-amino-alcohol in which the alcohol has been activated to form a leaving group suitable for nucleophilic substitution with inversion of stereochemistry at carbon (as described for Thiofoxins and Dimethylthiofoxins). Alternatively the β-amine can be condensed with an N-protected α-amino-aldehyde in the presence of a reducing agent forming an amine (according to J. Org. Chem., 2002, 67, 4017). The introduced nitrogen is here-on called the ω-amine group. This step introduces the R³/R⁴ functionality, depending on the selected β-aminoalcohol (possibly derived from an α-amino acid).

The ω-amine is then selectively deprotected and condensed with the carboxy ester (or after selective hydrolysis the corresponding carboxylic acid) to form a seven-membered ring (according to J. Med. Chem., 1987, 30, 1984).

Finally, the α-amine is selectively deprotected and acylated as described above to introduce the R¹ functionality.

In the fifth scheme (Scheme 3E below), the R³/R⁴ group(s) are introduced first, followed by cyclisation. The R¹ group and then the R² group are then introduced. Such a route would be optimal if greater diversity was to be introduced at R² than R¹ with least diversity at R³/R⁴.

Scheme 3E

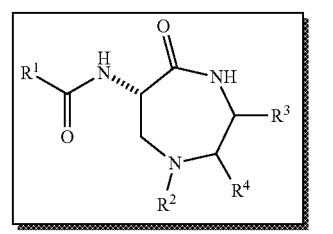

6-Acylamino-1-acyl/alkyl-1,4-diazepan-5-ones

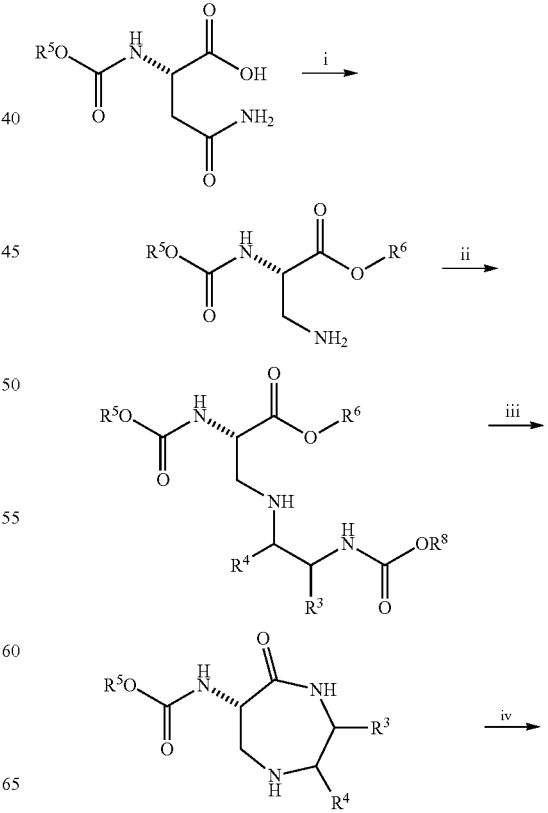

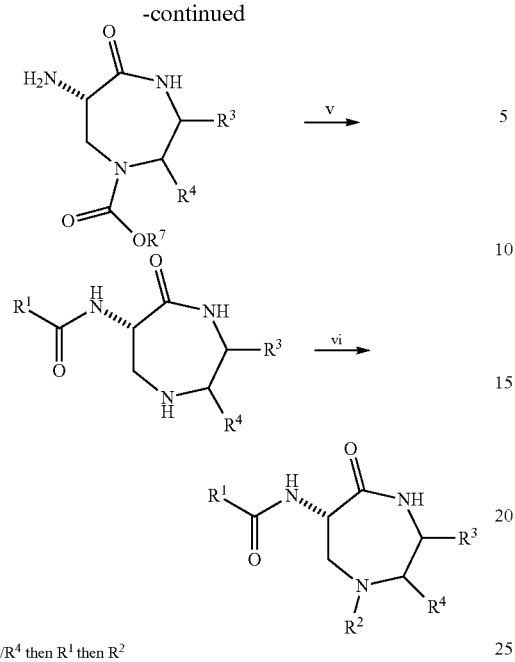

Introducing $R^3/R^4$ then $R^1$ then $R^2$

Reagents and conditions i) Hoffman degradation J. Org. Chem. 1997, 62 6918, then ester formation.
ii) Reductive amination of β-amine with protected amino aldehyde, see J. Org. Chem., 2002, 67, 4017 or alkylation with activated protected amino-alcohol.
iii) Selective deprotection and cyclisation in the style of J. Med. Chem. 1987, 30, 1984-1991.
iv) orthogonal protection of β-amine, then deprotection of α-amine by selective removal of $R^5OCO$ group.
v) acylation of α-amine, then selective deprotection of β-amine by removal of $R^7OCO$ group.
vi) Functionalisation of β–amine via alkylation, arylation or reductive alkylation, or acylation with activated acid, sulfonyl chloride, isocyanate, chloroformate, chloroformamide or peptide.

In this scheme, protected 3-aminoalanine is synthesised, for example by Hoffman degradation of N-α-protected asparagine, and the carboxylic acid esterified. Next, the β-amine is alkylated on nitrogen with an N-protected β-amino-alcohol in which the alcohol has been activated to form a leaving group suitable for nucleophilic substitution with inversion of stereochemistry at carbon (as described for Thiofoxins and Dimethylthiofoxins). Alternatively the β-amine can be condensed with an N-protected α-amino-aldehyde in the presence of a reducing agent forming an amine (according to J. Org. Chem., 2002, 67, 4017). The introduced nitrogen is here-on called the ω-amine group. This step introduces the $R^3/R^4$ functionality, depending on the selected β-aminoalcohol (possibly derived from an α-amino acid).

The ω-amine is then selectively deprotected and condensed with the carboxy ester (or after selective hydrolysis the corresponding carboxylic acid) to form a seven-membered ring (according to J. Med. Chem., 1987, 30, 1984). The secondary β-amine (now in the ring) is subsequently protected orthogonally to the α-amine.

Next, the α-amine is selectively deprotected and acylated as described above to introduce the $R^1$ functionality.

Finally the β-amine is deprotected and mono-alkylated, mono-arylated or sulfonated as required to introduce the $R^2$ functionality, using methods well known in the literature.

In the sixth scheme (Scheme 3F below), the $R^3/R^4$ group(s) are introduced first, followed by cyclisation. The $R^2$ group and then the $R^1$ group are then introduced. Such a route would be optimal if greater diversity was to be introduced at $R^1$ than $R^2$ with least diversity at $R^3/R^4$.

Scheme 3F

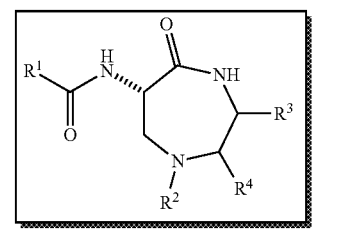

6-Acylamino-1-acyl/alkyl-1,4-diazepan-5-ones

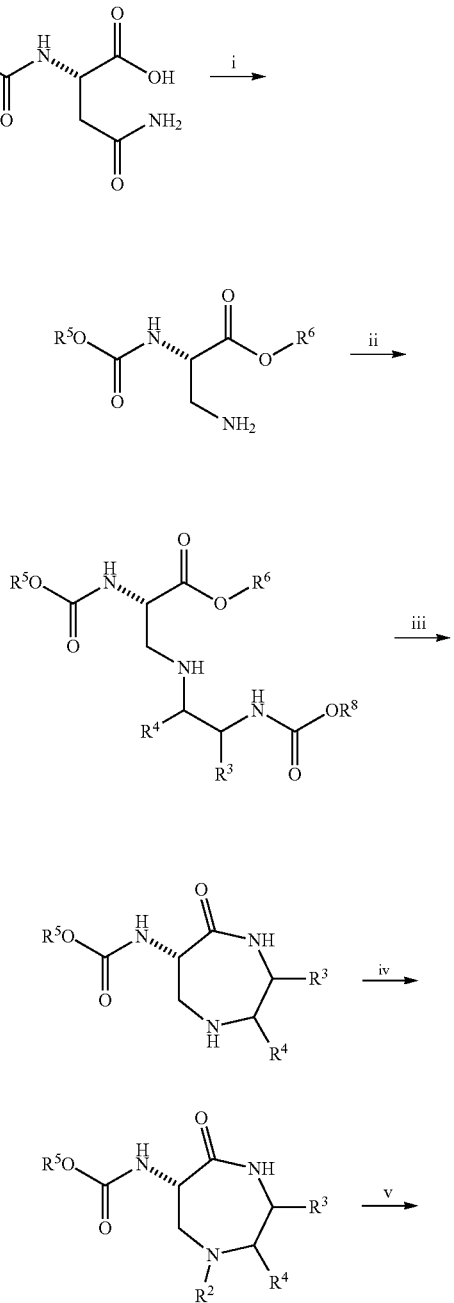

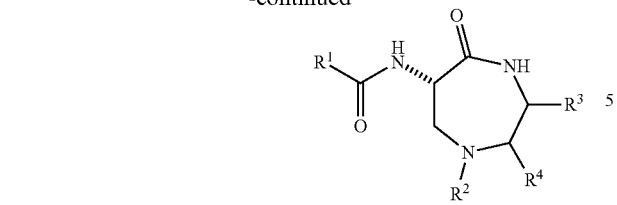

Introducing R³/R⁴ then R² then R¹
Reagents and conditions
i) Hoffman degradation J. Org. Chem. 1997, 62 6918, then ester formation.
ii) Reductive amination of β-amine with protected amino aldehyde, see J. Org. Chem., 2002, 67, 4017 or alkylation with activated protected amino-alcohol.
iii) Selective deprotection and cyclisation in the style of J. Med. Chem. 1987, 30, 1984-1991.
iv) Functionalisation of β-amine via alkylation, arylation or reductive alkylation, or acylation with setivated acid, sulfonyl chlorid, isocyanate, chloroformate, chloroformamide or peptide..
v) deprotection of α-amine by selective removal of R⁵OCO group then acylation of α-amine.

This scheme is very similar to Scheme 3E above, except that following the cyclisation step, the secondary β-amine (now in the ring), is alkylated, arylated or sulfonated, using methods well known in the literature, rather than being orthogonally protected. This introduces the R² functionality.

In the final step, the α-amine is then deprotected and acylated as described above to introduce the R¹ functionality.

These six schemes illustrate the facile nature of the synthesis of a library composed of one or more Azafoxin elements. In particular, the ability to perform the steps of the reaction in various orders in order to allow greater diversity to be introduced into different regions of the molecule while keeping the synthesis practicable is illustrated.

Example 4

Synthesis of Amidofoxins

The Amidofoxins are products of the coupling of 3-aminoalanine with an α-amino acid (as opposed to the coupling of 3-aminoalanine with a β-amino alcohol, possibly derived from an α-amino acid, which yields Azafoxins as described above). As with the Azafoxins, but not Thiofoxins and Dimethylthiofoxins, substitution at the ring heteroatom is possible (R²) to introduce further diversity. In the first scheme (Scheme 4A below), the R¹ group is introduced, followed by the R² group (substitution on nitrogen), then the R³ group, followed by cyclisation. Such a route would be optimal if greater diversity was to be introduced at R³ than R² with least diversity at R¹.

Scheme 4A

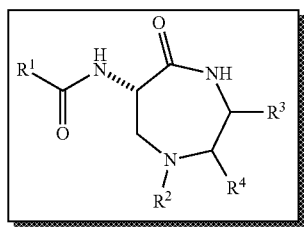

6-Acylamino-1-aryl/alkyl-1,4-diazepan-2,5-ones

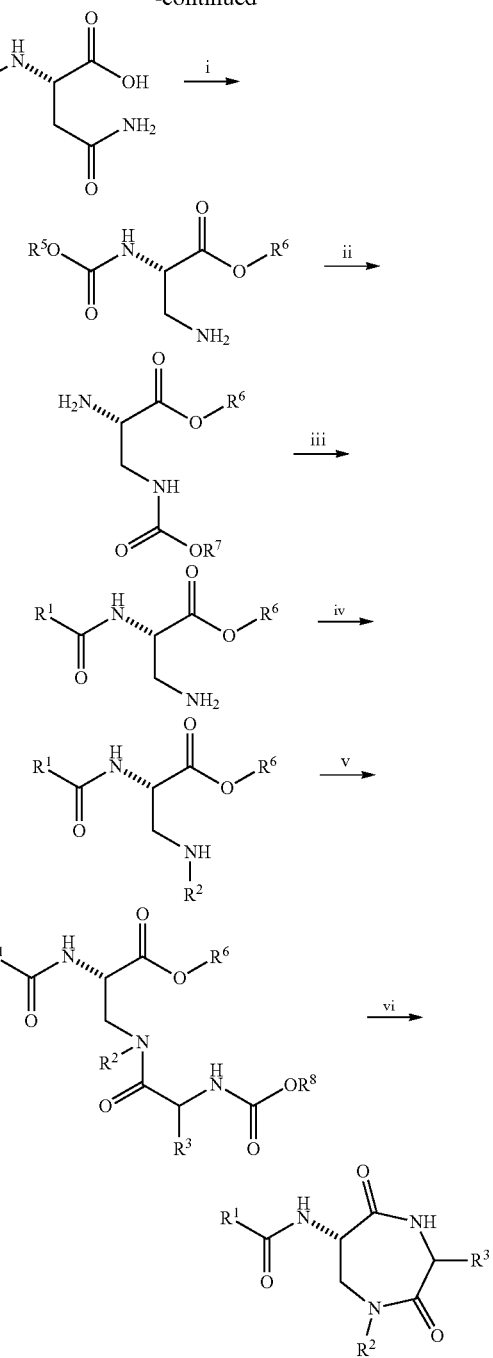

Introduction R¹ then R² then R³
Reagents and conditions
i) Hoffman degradation J. Org. Chem. 1997, 62 6918, then ester formation.
ii) orthogonal protection of β-amine, then deprotection of α-amine by selective removal of R⁵OCO group.
iii) acylation of α-amine, then selective deprotection of β-amine by removal of R⁷OCO group.
iv) Functionalisation of β–amine via alkylation, arylation or reductive alkylation.
v) acylation of β–amine with activated protected amino-acid.
vi) Selective deprotection and cyclisation in the style of J. Med. Chem. 1987, 30, 1984-1991.

As for Azafoxins, the first step is to synthesise a protected 3-amino alanine, for example by subjecting an N-α-carbamate ester protected asparagine to Hoffman degradation (according to J. Org. Chem., 1997, 62, 6918). The carboxylic acid group is then esterified, and the β-amine group protected orthogonally to the α-amine group.

In the next step, the α-amine is selectively deprotected and acylated as described above for Thiofoxins (for example in Scheme 1A). This introduces the $R^1$ functionality.

Next, the β-amine is also selectively deprotected, and mono-alkylated or mono-arylated as required, using methods well known in the literature, in order to introduce the $R^2$ functionality.

The secondary β-amine is then acylated with an N-protected α-amino-acid. The introduced nitrogen is here-on called the ω-amine group. It will be obvious than any of a range of suitable peptide coupling methods, well known in the literature, could be used to perform this step. This introduces the $R^3$ functionality, depending on the selection of the α-amino acid used in the reaction.

Finally, the ω-amine is selectively deprotected and condensed with the carboxy ester (or after selective hydrolysis the corresponding carboxylic acid) to form a seven-membered ring (for example, according to J. Med. Chem., 1987, 30, 1984).

In the second scheme (Scheme 4B below), the $R^2$ group is introduced, followed by the $R^1$ group (substitution on nitrogen), then the $R^3$ group, followed by cyclisation. Such a route would be optimal if greater diversity was to be introduced at $R^3$ than $R^1$ with least diversity at $R^2$.

Scheme 4B

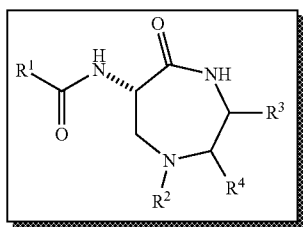

6-Acylamino-1-aryl/alkyl-1,4-diazepan-2,5-ones

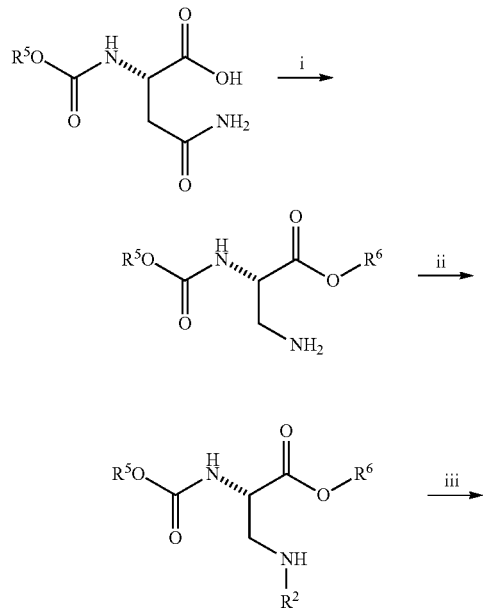

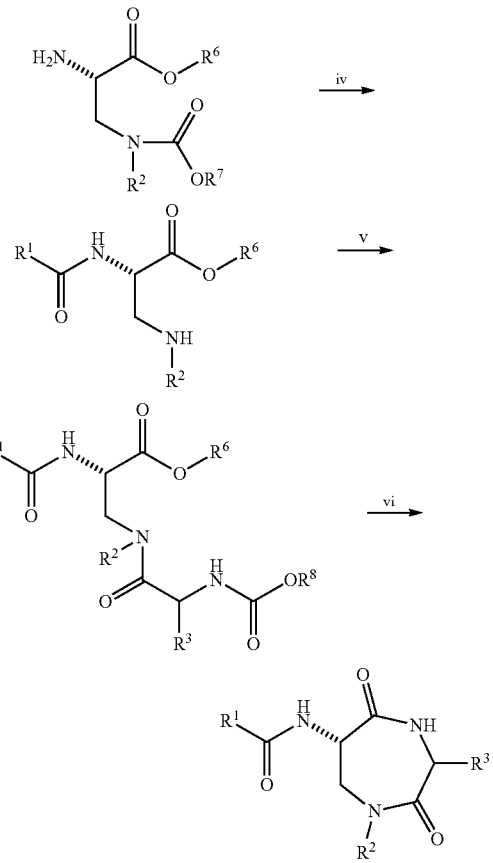

Introducing $R^2$ then $R^1$ then $R^3$
Reagents and conditions
i) Hoffman degradation J. Org. Chem. 1997, 62 6918, then ester formation.
ii) Functionalisation of β–amine via alkylation, arylation or reductive alkylation.
iii) orthogonal protection of β-amine, then deprotection of α-amine by selective removal of $R^5OCO$ group.
iv) acylation of α-amine, then selective deprotection of β-amine by removal of $R^7OCO$ group.
v) acylation of β–amine with activated protected amino-acid.
vi) Selective deprotection and cyclisation in the style of J. Med. Chem. 1987, 30, 1984-1991.

As in Scheme 4A, the first step is to synthesise a protected 3-aminoalanine, for example by subjecting an N-α-carbamate ester protected asparagine to Hoffman degradation (according to J. Org. Chem., 1997, 62, 6918). The carboxylic acid group is then esterified, but the β-amine is mono-alkylated or mono-arylated, using methods well known in the literature, prior to protecting the resulting secondary the β-amine group orthogonally to the α-amine. This introduces the $R^2$ functionality.

In the next step, the α-amine is selectively deprotected and acylated as described above. This introduces the $R^1$ functionality.

The secondary β-amine is then selectively deprotected and acylated with an N-protected α-amino-acid. The introduced nitrogen is here-on called the ω-amine group. It will be obvious than any of a range of suitable peptide coupling methods, well known in the literature, could be used to perform this step. This introduces the $R^3$ functionality, depending on the selection of the α-amino acid used in the reaction.

Finally, the ω-amine is selectively deprotected and condensed with the carboxy ester (or after selective hydrolysis the corresponding carboxylic acid) to form a seven-membered ring (for example, according to J. Med. Chem., 1987, 30, 1984).

In the third scheme (Scheme 4C below), the $R^2$ group is introduced, followed by the $R^3$ group. Following cyclisation, the $R^1$ group is then introduced. Such a route would be optimal if greater diversity was to be introduced at $R^1$ than $R^3$ with least diversity at $R^2$.

Scheme 4C

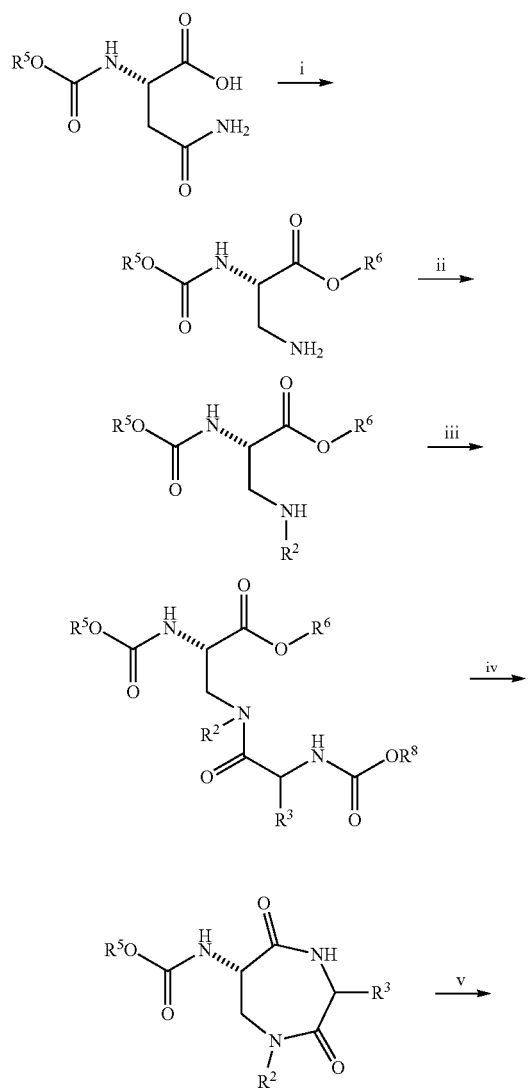

6-Acylamino-1-aryl/alkyl-1,4-diazepan-2,5-ones

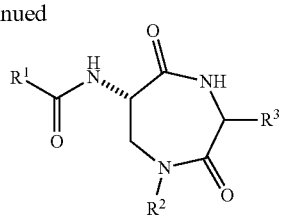

-continued

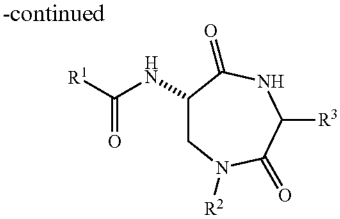

Introducing $R^2$ then $R^3$ then $R^1$
Reagents and conditions
i) Hoffman degradation J. Org. Chem. 1997, 62 6918, then ester formation.
ii) Functionalisation of β-amine via alkylation, arylation or reductive alkylation.
iii) Acylation of β-amine with activated protected amino-acid.
vi) Selective deprotection and cyclisation in the style of J. Med. Chem. 1987, 30, 1984-1991.
v) deprotection of α-amine by selective removal of $R^5OCO$ group and acylation of α-amine As in Scheme 4B, the first step is to synthesise a protected 3-aminoalanine, for example by subjecting an N-α-carbamate ester protected asparagine to Hoffman degradation (according to J. Org. Chem., 1997, 62, 6918). The carboxylic acid group is then esterified, and the β-amine is mono-alkylated or mono-arylated, using methods well known in the literature, introducing the $R^2$ functionality.

The secondary β-amine is then acylated with an N-protected α-amino-acid. The introduced nitrogen is here-on called the ω-amine group. It will be obvious than any of a range of suitable peptide coupling methods, well known in the literature, could be used to perform this step. This introduces the $R^3$ functionality, depending on the selection of the α-amino acid used in the reaction.

Next, the ω-amine is selectively deprotected and condensed with the carboxy ester (or after selective hydrolysis the corresponding carboxylic acid) to form a seven-membered ring (for example, according to J. Med. Chem., 1987, 30, 1984).

Finally, the α-amine is selectively deprotected and acylated as described above. This introduces the $R^1$ functionality.

These three schemes illustrate the facile nature of the synthesis of a library composed of one or more Amidofoxin elements. In particular, the ability to perform the steps of the reaction in various orders in order to allow greater diversity to be introduced into different regions of the molecule while keeping the synthesis practicable is illustrated.

A small number of members of the Amidofoxin class are already known. For example, see J. Org. Chem. (2003) 68:7893. However, these examples are restricted to $R^3$=benzyl or $CH_2CH_2COR'$ (where R' is variable), and they were not tested for activity as GPCR ligands." Other related structures in the public domain, such as the antibiotic TAN1057C (VII), are not Amidofoxins and would not fall under the scope of the present invention because of the absence of a 3-acylamino or 3-sulfonamide substituent on the ring as well as the presence of substitution at N1.

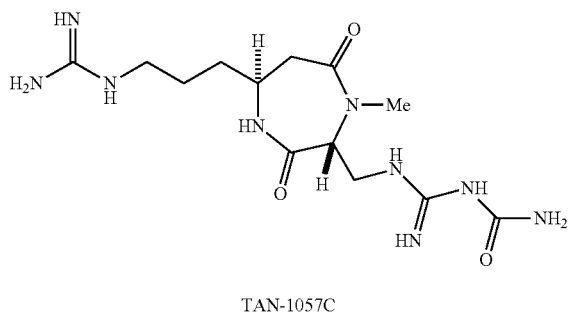

(VII)

TAN-1057C

Pharmacological Study of the Products of the Invention
Principle of the Assays
A: GPCR Antagonism In principle, a compound of the invention can be tested for antagonist activity at a given GPCR by exposing the receptor to a labelled ligand under appropriate conditions for binding, in the absence and presence of various concentrations of the test compound. The amount of label associated with the receptor is then quantitated. If the test compound is able to compete with the labelled ligand for binding then the amount of label associated with the receptor will decrease with increasing concentration of the test compound. From the plot of ligand bound against test compound concentration it is possible to estimate the binding affinity of the test compound to the receptor.

Such an assay therefore requires:

(1) A source of the GPCR of interest. The sequence of every member of the GPCR superfamily from humans is now available from the human genome sequence. Such sequences can be cloned into a suitable vector and expressed in a suitable cell type (for example, Jurkat T cells which are already known to express virtually no endogenous GCPRs with the exception of the chemokine receptor CXCR4). After selection using an antibiotic appropriate to the vector used, stable cell lines expressing high levels of the chosen GPCR can be established.

Membrane fractions from cell lines expressing the chosen GPCR can be prepared using a range of methods well known in the art. For example, according to Kuo et al. (Proc. Natl. Acad. Sci. USA (1980) 77:7039), the cells may be resuspended in 25 mM HEPES buffer pH7.5 containing 0.25M sucrose, 2.5 mM $MgCl_2$, 2.5 mM EGTA and 50 mM β-mercaptoethanol, as well as protease inhibitors such as PMSF and leupeptin and split open using a Dounce homogeniser. The suspension is then subjected to centrifugation at 120×g to pellet unbroken cells and large cellular fragments, and the supernatant containing small membrane fragments and cytosolic components is retained. This supernatant is then subjected to ultracentrifugation at 100,000×g, producing a pellet of membrane fragments enriched in the chosen GPCR. The pellet is resuspended in an appropriate binding buffer, and the total protein concentration determined using, for example, a commercially available protein assay such as Coomassie Plus (Pierce). The membrane preparation can be adjusted in volume to yield a standardised total protein concentration, for example of 1 mg/ml. The standardised preparation can be stored at −85° C. in aliquots until required.

(2) A labelled ligand with high affinity for the chosen GPCR. Suitable ligands for most GPCRs are well known in the literature. Such ligands may be the natural ligand for the receptor (for example, dopamine) or it may be a pharmacological tool (such as domperidone). A list of suitable ligands for a wide range of commonly investigated GPCRs is provided in Table 1, but it will be obvious to those skilled in the art that other suitable ligands exist for many of these receptors. Ligands most useful for this purpose will have an affinity constant for binding to the chosen receptor of at least 1 µM, and preferably less than 100 nM, and more preferably less than 10 nM.

TABLE 1

| Receptor | Radioligand | Conc (nM) | Competitor | Conc (µM) |
|---|---|---|---|---|
| Adenosine $A_1$ | [$^3$H]DPCPX | 1 | DPCPX | 1 |
| Adenosine $A_2$ | [$^3$H]CGS 21680 | 6 | NECA | 10 |
| Adenosine $A_3$ | [$^{125}$I]AB-MEGA | 0.1 | IB-MEGA | 1 |
| $α_1$-adrenoceptor | [$^3$H]prazosin | 0.25 | prazosin | 0.5 |
| $α_1$-adrenoceptor | [$^3$H]RX 821002 | 0.5 | (-)-epinephrine | 100 |
| $β_1$-adrenoceptor | [$^3$H](-)-CGP 12177 | 0.15 | alprenolol | 50 |
| $β_2$-adrenoceptor | [$^3$H](-)-CGP 12177 | 0.15 | alprenolol | 50 |
| Angiotensin $AT_1$ | [$^{125}$I][sar$^1$, ile$^8$]-AII | 0.05 | angiotensin II (AII) | 10 |
| Angiotensin $AT_2$ | [$^{125}$I] CGP 42112A | 0.05 | angiotensin II (AII) | 1 |
| Central BZD | [$^3$H] flunitrazepam | 0.4 | diazepam | 3 |
| Peripheral BZD | [$^3$H]PK 11195 | 0.2 | PK 11195 | 10 |
| Bombesin (ns) | [$^{125}$I][Tyr$^4$]bombesin | 0.01 | bombesin | 1 |
| Bradykinin $B_2$ | [$^3$H]bradykinin | 0.2 | bradykinin | 1 |
| CGRP receptor | [$^{125}$I]hCGRPα | 0.03 | hCGRPα | 1 |
| Cannabinoid $CB_1$ | [$^3$H]WIN 55212-2 | 2 | WIN 55212-2 | 10 |
| Cholecystekinin A | [$^{125}$I]CCK-8 | 0.08 | CCK-8 | 1 |
| Cholecystekinin B | [$^{125}$I]CCK-8 | 0.025 | CCK-8 | 1 |
| Dopamine D1 | [$^3$H]SCH 23390 | 0.3 | SCH 23390 | 1 |
| Dopamine D2s | [$^3$H]spiperone | 0.3 | (+)-butaclamol | 10 |
| Dopamine D3 | [$^3$H]spiperone | 0.3 | (+)-butaclamol | 10 |
| Dopamine D4.4 | [$^3$H]spiperone | 0.3 | (+)-butaclamol | 10 |
| Dopamine D5 | [$^3$H]-SCH 23390 | 0.3 | SCH 23390 | 10 |
| Endothelin $ET_A$ | [$^{125}$I]endothelin-1 | 0.03 | endothelin-1 | 0.1 |
| Endothelin $ET_B$ | [$^{125}$I]endothelin-1 | 0.03 | endothelin-1 | 0.1 |
| GABA (ns) | [$^3$H]-GABA | 10 | GABA | 100 |
| Galanin GAL1 | [$^{125}$I]galanin | 0.03 | galanin | 1 |
| Galanin GAL2 | [$^{125}$I]galanin | 0.05 | galanin | 1 |
| IL8RB (CXCR2) | [$^{125}$I]IL-8 | 0.025 | IL-8 | 0.3 |
| CCR1 | [$^{125}$I]MIP1α | 0.03 | MIP1α | 0.1 |
| Histamine $H_1$ | [$^3$H]pyrilamine | 3 | pyrilamine | 1 |
| Histamine $H_2$ | [$^{125}$I]APT | 0.2 | tiotidine | 100 |
| MC4 | [$^{125}$I]NDP-α-MSH | 0.05 | NDP-α-MSH | 1 |
| Melatonin $ML_1$ | [$^{125}$I] iodomelatonin | 0.025 | melatonin | 1 |
| Muscarinic $M_1$ | [$^3$H]pirenzepine | 2 | atropine | 1 |
| Muscarinic $M_2$ | [$^3$H]AF-DX 384 | 2 | atropine | 1 |
| Muscarinic $M_3$ | [$^3$H]4-DAMP | 0.2 | atropine | 1 |
| Muscarinic $M_4$ | [$^3$H]4-DAMP | 0.2 | atropine | 1 |
| Muscarinic $M_5$ | [$^3$H]4-DAMP | 0.2 | atropine | 1 |
| Neurokinin $NK_1$ | [$^{125}$I][sar$^9$,met$^{11}$]-SP | 0.15 | [sar$^9$,met$^{11}$]-SP | 1 |
| Neurokinin $NK_2$ | [$^{125}$I]NKA | 0.1 | [nle$^{10}$]-NKA (4-10) | 10 |
| Neurokinin $NK_3$ | [$^3$H]SR 142801 | 0.2 | SB 222200 | 10 |
| Neuropeptide $Y_1$ | [$^{125}$I]peptide YY | 0.05 | NPY | 1 |
| Neuropeptide $Y_2$ | [$^{125}$I]peptide YY | 0.015 | NPY | 1 |
| Neurotensin $NT_1$ | [$^{125}$I][Tyr$^3$]-neurotensin | 0.02 | neurotensin | 1 |
| δ opioid (δ$_2$) | [$^3$H]DADLE | 0.5 | naltrexone | 10 |
| κ opioid | [$^3$H]U 69593 | 0.7 | naloxone | 10 |
| µ opioid | [$^3$H]DAMGO | 0.5 | naloxone | 10 |
| ORL1 opioid | [$^3$H]nociceptin | 0.2 | nociceptin | 1 |
| PACAP | [$^{125}$I]PACAP(1-27) | 0.02 | PACAP(1-27) | 0.1 |
| Purine P2X | [$^3$H]α,β-MeATP | 3 | α,β-MeATP | 10 |
| Purine P2Y | [$^{35}$S]dATPαS | 10 | dATPαS | 10 |
| Serotonin $5HT_{1A}$ | [$^3$H]8-OH-DPAT | 0.5 | 8-OH-DPAT | 10 |
| Serotonin $5HT_{1B}$ | [$^{125}$I]CYP | 0.1 | serotonin | 10 |
| Serotonin $5HT_{2A}$ | [$^3$H]ketanserin | 0.5 | ketanserin | 1 |

TABLE 1-continued

| Receptor | Radioligand | Conc (nM) | Competitor | Conc (μM) |
|---|---|---|---|---|
| Serotonin 5HT$_{2c}$ | [$^3$H]mesulurgine | 1 | SB 242084 | 10 |
| Serotonin 5HT$_3$ | [$^3$H]BRL 43694 | 0.5 | MDL 72222 | 10 |
| Serotonin 5HT$_{5A}$ | [$^3$H]LSD | 1 | serotonin | 100 |
| Serotonin 5HT$_6$ | [$^3$H]LSD | 2 | serotonin | 100 |
| Serotonin 5HT$_7$ | [$^3$H]LSD | 4 | serotonin | 10 |
| Sigma receptor (ns) | [$^3$H]DTG | 8 | haloperidol | 10 |
| Somatostatin (ns) | [$^{125}$I][Tyr$^{11}$]-sst14 | 0.05 | sst14 | 0.3 |
| Vasopressin VIP$_1$ | [$^{125}$I]VIP | 0.04 | VIP | 0.3 |

Abbreviation used: (ns) = non-selective

Once the ligand has been selected, it will likely be necessary to label the ligand so that subsequently the amount bound to the chosen GPCR can be determined (although it may be possible to perform an assay without labelling the ligand, providing that a sensitive and accurate method of determining the amount of unbound ligand is available—for example it may be possible to use an ELISA assay to measure unbound ligand, and by inference calculate the amount of bound ligand). Appropriate methods of labelling the ligand vary depending on the nature of the ligand: small molecules may be most readily labelled with a radionuclide such as $^3$H, $^{14}$C or $^{35}$S; peptides may be most readily labelled with a co-synthetic biotin (and subsequently with labelled streptavidin), with fluorescent tags (such as fluorescein isothiocyanate) or with radionuclides (such as $^{125}$I-iodination of tyrosine residues in the peptide); proteins may be most readily labelled with fluorescent tags (such as fluorescein isothiocyanate) or with radionuclides (such as $^{125}$I-iodination of tyrosine residues in the protein).

The extent of the labelling (that is, the proportion of molecules in the sample bearing the label) must be sufficient that the amount of ligand binding to the receptor can be conclusively quantitated.

With these two components it is then possible to test whether the compounds of the invention modulate ligand binding to any given GPCR, using methods well known in the art. For example, in a series of tubes the membrane preparation is mixed with the radioligand at a concentration near to the affinity constant for the binding of the ligand to the chosen GPCR. In some tubes, the compound of the invention is also added at various concentrations. In yet other tubes a positive control inhibitor is added (which may be a large excess of the same ligand as the radioligand but in the absence of the radionuclide tag). Typically, three tubes would be prepared under each set of conditions. The tubes are then incubated, typically at between 4° C. and 37° C., more typically at room temperature for a period of time to allow an equilibrium to be reached between free and bound radioligand. Typically, this will take from between 20 minutes and 4 hours, and the period required for any given set of reaction conditions can be determined by methods well known in the art (for example, by performing a time-course experiment). Once equilibrium is achieved, it is necessary to determine the amount of radioligand bound. For example, the membrane-bound receptor (plus any bound radioligand) can be separated from free radioligand in solution by filtration through filters (such as GF/C filters treated with 1% polyethyleneimine). The filters may then be air-dried and subjected to scintillation counting to determine the fraction of the radioligand added which is now bound to the receptor.

Alternatively, the compounds of invention may be subjected to screening using commercially available receptor screening procedures (for example, the services offered by Cerep, 128 Rue Danton, Paris, France). Such services readily identify members of a library, such as the library provided for in the invention, which modulate ligand binding to one or more GPCRs.

Compounds identified as modulating ligand binding to one or more GPCRs using the methods outlined above will usually be full antagonists. However, it is necessary to perform functional assays in order to confirm the antagonist properties of the compound. For example, depending on the GPCR and/or the ligand used certain second messenger signals will be stimulated (or inhibited) in order to transduce the signal that the ligand is present. Cells may show an increase (or a decrease) in the cellular concentration of cyclic adenosine monophosphate (cAMP), various phosphorylated inositol-containing compounds (including I(1,4,5)P3 and I(1,3,5)P3), calcium ions, polyadenosine or other intracellular messengers known in the art, in response to presentation of the ligand. Full antagonists will abrogate the change in intracellular messengers caused by the natural ligand(s), and have no effect in the absence of natural ligand. In marked contrast, full agonists will have no effect when added with the natural ligand(s), but mimic the changes in intracellular messengers caused by the natural ligand(s) when added in the absence of natural ligand. Some compounds, including compounds of the invention may be partial antagonists, partial agonists or mixed agonist/antagonists depending on the pattern of effects on intracellular messengers. Despite the complex pharmacological definition of such compounds, they may have useful therapeutic properties in certain diseases, and a number of well established human pharmaceuticals are known to be partial agonists, partial antagonists or mixed agonist/antagonists at one or more GPCRs.

B: GPCR Agonism

It is inherently considerably more difficult to test for agonist activity than antagonist activity, particularly using high throughput screening techniques. The compounds of the invention are, therefore, likely to be particularly useful in the search for agonists than general lead discovery libraries because of the higher incidence of GPCR agonists among the library elements.

A test for a GPCR agonist, in principle, requires a cell or organ culture system which responds to a natural ligand of the chosen GPCR(s) with a desirable biochemical or physiological response. Examples of such a response include, but are not limited to, changes in intracellular messengers (such as cAMP, IP(1,4,5)P3, calcium ions or polyadenosine), changes in enzyme activity (such as activation of protein kinases, phosphatases, metabolic enzymes or transport proteins), changes in gene expression patterns, altered phagocytosis, altered protein secretion, altered rate of proliferation, contraction of muscle cells/tissue, neurotransmission and so forth. Since responses such as these are inherently more complex to measure than the binding of natural ligand(s) to chosen GPCRs, this is why assays for GPCR agonists are more challenging than for antagonists.

The general method required to test whether a compound of the invention is an agonist at one or more chosen GPCRs is well established in the art. Cells are exposed to various concentrations of the test compound, for example, by addition of the compound in a suitable vehicle (such as DMSO, ethanol or methanol) at various concentrations (for example, from about 0.1 nM to about 10 mM) in the cell culture medium for period of time (for example, from 1 minute to 48 hours, depending on the timecourse of the response to be measured), typically at 37° C. In parallel cells are also exposed to the natural ligand, and left unexposed to any additional compound(s) (as control cells). At the end of the incubation period, a response known in the art to occur in response to the natural ligand binding to the chosen GPCR(s) is measured. If the compound of the invention is an agonist at the chosen GPCRs, then the responses to the test compound (at certain concentrations) will be qualitatively similar to the response to the natural ligand.

Examples of suitable assay systems for agonists at particular GPCRs follow:

Somatostatin is an agonist at the sstr2 and sstr5 receptors such that it inhibits the secretion of growth hormone by isolated pituitary cells. To determine whether compounds of the invention are agonists at sstr2 and/or sstr5, rat pituitary cells are isolated and placed into culture. The cells are then incubated alone, or in the presence of somatostatin at 33 nM, or in the presence of the test compound(s) at various concentrations from about 0.1 nM to about 10 mM at 37° C. for 24 hours. At the end of the experiment, the cell culture medium is removed, clarified by centrifugation and subjected to an assay for growth hormone (GH), for example by performing a commercially available ELISA or radioimmunoassay. The cells exposed to somatostatin will have produced between 30% and 90% less GH than cells incubated alone. If the compound of the invention is an agonist at the somatostatin receptors, then the level of GH will be lower in the medium from cells exposed to the test compound (at least at certain concentrations) than in the medium from cells incubated alone. Typically, medium is collected from three replicate wells containing cells treated identically under each of the conditions of the experiment, so that an appropriate statistical test (such as an ANOVA or unpaired Student's t-test) can be used to demonstrate that the test compound produced a statistically significant reduction in GH secretion, and therefore likely possesses agonist activity at the chosen receptors, sstr2 and/or sstr5.

Endothelin-1 is a peptide which signals through the ET-A and/or ET-B receptor to cause vasoconstriction. To determine whether compounds of the invention are agonists at ET-A and/or ET-B, rings of human aorta (obtained from transplant donor hearts) can be put into organ culture. Rings are then exposed either to increasing concentrations of Endothelin-1 (from 0.01 nM to 100 nM), or to increasing concentrations of the test compound(s) (from about 0.1 nM to about 10 mM) at 37° C., raising the concentration of the appropriate agent approximately every 5 minutes. Throughout the experiment the contraction of the aortic ring is measured by a strain gauge designed and commercially available for such a purpose. The rings exposed to endothelin-1 will contract as the concentration of endothelin-1 is increased, so that by the time the top concentration is reached the force exerted on the strain gauge will be significantly higher than prior to addition of endothelin-1. If the compound of the invention is an agonist at the endothelin receptors, then the force exerted on the strain guage will also be higher (at least at certain concentrations) than prior to addition of the test compound. Typically, three or more separate aortic rings are treated with increasing concentrations of the same agent under identical experimental conditions, so that an appropriate statistical test (such as an ANOVA or unpaired Student's t-test) can be used to demonstrate that the test compound produced a statistically significant increase in aortic contraction, and therefore likely possesses agonist activity at the chosen receptors, ET-A and/or ET-B.

The chemokine SDF-1a is a peptide which signals through the CXCR4 receptor to cause leukocyte migration. To determine whether compounds of the invention are agonists at CXCR4 cultured human immortalised T-cells (Jurkat T cells, for example), are placed in the top well of a purpose-built commercially available transwell migration apparatus. Replicate wells are then exposed to lower chambers containing only culture medium, or to lower chambers containing SDF-1a at 75 nM, or to lower chambers containing various concentrations of the test compound(s) (from about 0.1 nM to about 10 mM) and incubated for a period of time (typically between 30 minutes and 3 hours) at 37° C. At the end of the incubation, the number of cells present in the lower chamber is a measure of the amount of migration occurring. The number of cells in the lower chamber may be counted by direct visualisation, or by various well-known methods such as incubation with MTT dye which is converted to an insoluble blue formazan product in proportion to the number of cells present. In wells exposed to a lower chamber containing SDF-1a, the number of cells in the lower chamber will be between 2-fold and 10-fold higher than the number of cells in lower chambers containing culture medium alone. If the compound of the invention is an agonist at CXCR4, then the number of cells in the lower chambers containing the test compound(s) will also be higher (at least at certain concentrations) than in the lower chambers containing medium alone. Typically, three or more separate chambers are treated identically under each of the experimental conditions, so that an appropriate statistical test (such as an ANOVA or unpaired Student's t-test) can be used to demonstrate that the test compound produced a statistically significant increase in leukocyte migration, and therefore likely possesses agonist activity at the chosen receptor, CXCR4.

The bioactive amine adrenalin increases the intracellular concentration of cAMP in vascular smooth muscle cells. To determine whether compounds of the invention are agonists at β-adrenoreceptors, rat vascular smooth muscle cells from thoracic aorta are isolated and placed into culture. The cells are then incubated alone, or in the presence of the adrenalin agonist salbutamol at 33 nM, or in the presence of the test compound(s) at various concentrations from about 0.1 nM to about 10 mM at 37° C. for 15 minutes. At the end of the experiment, the cell culture medium is removed, the cells are washed three times in ice cold buffer and then lysed in an appripriate lysis buffer, prior to measurement of the intracellular concentration of cAMP, for example by performing a commercially available ELISA or radioimmunoassay. The cells exposed to salbutamol will have an intracellular cAMP concentration between 15% and 150% higher than cells exposed to medium alone. If the compound of the invention is an agonist at the β-adrenoreceptors, then the intracellular concentration of cAMP will be higher in the cells exposed to the test compound (at least at certain concentrations) than in the cells incubated alone. Typically, cell lysate is prepared from three replicate wells containing cells treated identically under each of the conditions of the experiment, so that an appropriate statistical test (such as an ANOVA or unpaired Student's t-test) can be used to demonstrate that the test compound produced a statistically significant increase in intracellular cAMP concentration, and therefore likely possesses agonist activity at the chosen β-adrenoreceptors.

It will be obvious that assays such as the examples above will identify agonists at the chosen GPCRs, and distinguish the compounds of the invention from inactive compounds and from compounds with antagonist or partial antagonist activity at the chosen GPCR, but will not necessarily uniquely identify the chosen GPCR as the molecular target of the compound of the invention. For example, a compound of the invention demonstrated to elevate cAMP in vascular smooth muscle cells to the same extent as the β-adrenoreceptor agonist salbutamol, may be an agonist at the β-adrenoreceptor GPCRs, or it may be an agonist at another GPCR which also elevates cAMP (such as dopamine D2 receptor). Alternatively, a compound of the invention which stimulates the migration of leukocytes to a similar extent to SDF-1a may be an agonist at CXCR4, or it may be an agonist at another GPCR which stimulates leukocyte migration (such as the C5a receptor). Validation of the molecular target GPCR at which compounds of the invention act as an agonist will require the performance of additional experiments using specific antagonists already identified against the chosen GPCR, or the use of recombinant cell lines expressing only the chosen GPCR. For example, if the leukocyte migration induced by a compound of the invention were inhibited by the addition of the CXCR4-specific antagonist AMD3100 at an appropriate concentration, then it would be reasonable to conclude that CXCR4 was the molecular target of the compound of the invention. Similarly, if the leukocyte migration induced by a compound of the invention was observed using a cell line expressing CXCR4, but absent in the same cell line not expressing CXCR4, then it would be reasonable to conclude that CXCR4 was the molecular target of the compound of the invention.

The invention claimed is:

1. A compound of general formula (III)

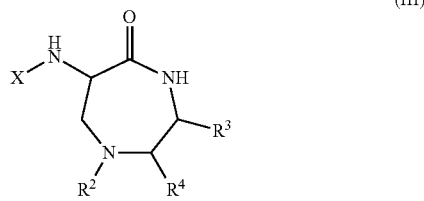

(III)

wherein:

X is —CO—$(Y)_k$—$(Z)_n$ or $SO_2$—$(Y)_k$—$(Z)_n$;

k is 0 or 1;

Y is a cycloalkyl or polycyloalkyl group;

or Y is a cycloalkenyl or polycycloalkenyl group;

each Z is independently selected from hydrogen, or an alkyl, haloalkyl, alkoxy, haloalkoxy, alkenyl, alkynyl, alkylamino, alkylaminoalkyl, alkylaminodialkyl, charged alkylaminotrialkyl or charged alkylcarboxylate radical of 1 to 20 carbon atoms;

or each Z is independently selected from fluoro, chloro, bromo, iodo, hydroxy, oxyalkyl, amino, aminoalkyl, aminodialkyl, charged aminotrialkyl, or carboxylate radical; and n is any integer from 1 to m, where m is the maximum number of substitutions permissible on the cyclo-group Y; or each Z may be independently a peptido radical; and wherein $R^2$ is an alkyl, aryl or an acyl group;

and wherein $R^3$ is a side-chain of an α-amino acid used in formation of (III);

and wherein $R^4$ is a 2-substituent of a β-amino alcohol used in formation of (III).

2. A compound according to claim 1 wherein the carbon atom of the Y-group of the —$(Y)_k$—$(Z)_n$ radical which is bonded to the exocyclic amine group is a key carbon which is di-substituted with the same or different groups selected from: alkyl, haloalkyl, alkoxy, haloalkoxy, alkenyl, alkynyl, and alkylamino radicals.

3. A compound according to claim 2 wherein the key carbon is chiral.

4. A compound according to claim 2 wherein the key carbon has sp3 hybridised bonds.

5. A compound according to claim 2 wherein the key carbon has essentially tetrahedral bond angles.

6. A compound according to claim 2 wherein the ring or rings of Y constrain the bond angles at the key carbon to be essentially tetrahedral.

7. A method of identifying one or more agent(s) which modulate signalling through GPCRs, the method comprising:
screening members of a library comprising two or more compounds according to claim 1 for antagonist or agonist activity at a GPCR, thereby identifying one or more of said members as agent(s) which modulate signalling through GPCRs.

8. A method according to claim 7, where the agent(s) identified are antagonists at one or more GPCRs.

9. A method according to claim 7 where the agent(s) identified are agonists at one or more GPCRs.

10. A method according to claim 7 where the GPCR is selected from the group consisting of: adrenalin receptors, endothelin receptors, chemokine receptors, EDG receptors, VIP/PECAP receptors, dopamine receptors, serotonin receptors, purine receptors, metabotropic glutamate receptors, acetyl choline receptors, C5a receptors, fMLP receptors, glucagon or GLP receptors, NPY receptors, MSH receptors, glycoprotein hormone receptors, protease activated receptors (PARs), somatostatin receptors, angiotensin receptors, cholecystokinin receptors, and melatonin receptors.

11. The method according to claim 7 further comprising:
synthesising a carbon analogue of said agent, wherein the heteroatom in the lactam ring is replaced by —$CH_2$—; and providing said carbon analogue (or a pharmaceutically acceptable salt thereof) in isolated and purified form.

12. A method for preparing a library of compounds enriched in GPCR antagonists and/or GPCR agonists, the method comprising:
preparing an acylaminolactam library comprising two or more compounds of claim 1 by reacting a diversity of α-amino acids and/or β-amino alcohols with an acylamino acid.

* * * * *